United States Patent
Bruce et al.

(10) Patent No.: US 10,274,550 B2
(45) Date of Patent: Apr. 30, 2019

(54) HIGH SPEED SEQUENTIAL CANCELLATION FOR PULSED MODE

(71) Applicant: Lockheed Martin Corporation, Bethesda, MD (US)

(72) Inventors: Gregory Scott Bruce, Abington, PA (US); Peter G. Kaup, Marlton, NJ (US); Arul Manickam, Mount Laurel, NJ (US)

(73) Assignee: LOCKHEED MARTIN CORPORATION, Bethesda, MD (US)

( * ) Notice: Subject to any disclaimer, the term of this patent is extended or adjusted under 35 U.S.C. 154(b) by 43 days.

(21) Appl. No.: 15/468,397

(22) Filed: Mar. 24, 2017

(65) Prior Publication Data

US 2018/0275223 A1  Sep. 27, 2018

(51) Int. Cl.
*G01V 3/00* (2006.01)
*G01R 33/26* (2006.01)
*G01R 33/032* (2006.01)
*G01R 33/60* (2006.01)

(52) U.S. Cl.
CPC .......... *G01R 33/26* (2013.01); *G01R 33/032* (2013.01); *G01R 33/60* (2013.01)

(58) Field of Classification Search
USPC ...................................................... 324/301
See application file for complete search history.

(56) References Cited

U.S. PATENT DOCUMENTS

| | | | |
|---|---|---|---|
| 2,746,027 A | 5/1956 | Murray | |
| 3,359,812 A | 12/1967 | Everitt | |
| 3,389,333 A | 6/1968 | Wolff et al. | |
| 3,490,032 A | 1/1970 | Zurflueh | |
| 3,514,723 A | 5/1970 | Cutler | |
| 3,518,531 A | 6/1970 | Huggett | |

(Continued)

FOREIGN PATENT DOCUMENTS

| | | |
|---|---|---|
| CN | 105738845 A | 7/2016 |
| CN | 106257602 | 12/2016 |

(Continued)

OTHER PUBLICATIONS

Teeling-Smith et al., "Electron Paramagnetic Resonance of a Single NV Nanodiamond Attached to an Individual Biomolecule", Biophysical Journal 110, May 10, 2016, pp. 2044-2052.

(Continued)

*Primary Examiner* — Rodney E Fuller
(74) *Attorney, Agent, or Firm* — Foley & Lardner LLP

(57) ABSTRACT

Magnetometers with high bandwidth acquisition of data with increased sensitivity are described herein. Increased bandwidth and sensitivity may be achieved by eliminating a reference signal for full repolarization of the magneto-optical defect center material prior to acquisition. Elimination of the reference signal eliminates the time needed to repolarize the magneto-optical defect center material and the acquisition time for the reference signal. A radiofrequency (RF) pulse sequence may be activate to apply an RF field to the magneto-optical defect center material and a magnetic field measurement may be acquired using the magneto-optical defect center material. The magnetic field measurement may be acquired independent of a reference magnetic field measurement.

20 Claims, 7 Drawing Sheets

(56) References Cited

U.S. PATENT DOCUMENTS

| | | |
|---|---|---|
| 3,621,380 A | 11/1971 | Barlow, Jr. |
| 3,745,452 A | 7/1973 | Osburn et al. |
| 3,899,758 A | 8/1975 | Maier et al. |
| 4,025,873 A | 5/1977 | Chilluffo |
| 4,047,805 A | 9/1977 | Sekimura |
| 4,078,247 A | 3/1978 | Albrecht |
| 4,084,215 A | 4/1978 | Willenbrock |
| 4,322,769 A | 3/1982 | Cooper |
| 4,329,173 A | 5/1982 | Culling |
| 4,359,673 A | 11/1982 | Bross et al. |
| 4,368,430 A | 1/1983 | Dale et al. |
| 4,410,926 A | 10/1983 | Hafner et al. |
| 4,437,533 A | 3/1984 | Bierkarre et al. |
| 4,514,083 A | 4/1985 | Fukuoka |
| 4,588,993 A | 5/1986 | Babij et al. |
| 4,636,612 A | 1/1987 | Cullen |
| 4,638,324 A | 1/1987 | Hannan |
| 4,675,522 A | 6/1987 | Arunkumar |
| 4,768,962 A | 9/1988 | Kupfer et al. |
| 4,818,990 A | 4/1989 | Fernandes |
| 4,820,986 A | 4/1989 | Mansfield et al. |
| 4,945,305 A | 7/1990 | Blood |
| 4,958,328 A | 9/1990 | Stubblefield |
| 4,982,158 A | 1/1991 | Nakata et al. |
| 5,019,721 A | 5/1991 | Martens et al. |
| 5,038,103 A | 8/1991 | Scarzello et al. |
| 5,113,136 A | 5/1992 | Hayashi et al. |
| 5,134,369 A | 7/1992 | Lo et al. |
| 5,189,368 A | 2/1993 | Chase |
| 5,200,855 A | 4/1993 | Meredith et al. |
| 5,210,650 A | 5/1993 | O'Brien et al. |
| 5,245,347 A | 9/1993 | Bonta et al. |
| 5,252,912 A | 10/1993 | Merritt et al. |
| 5,301,096 A | 4/1994 | Klontz et al. |
| 5,384,109 A | 1/1995 | Klaveness et al. |
| 5,396,802 A | 3/1995 | Moss |
| 5,420,549 A | 5/1995 | Prestage |
| 5,425,179 A | 6/1995 | Nickel et al. |
| 5,427,915 A | 6/1995 | Ribi et al. |
| 5,548,279 A | 8/1996 | Gaines |
| 5,568,516 A | 10/1996 | Strohallen et al. |
| 5,586,069 A | 12/1996 | Dockser |
| 5,597,762 A | 1/1997 | Popovici et al. |
| 5,638,472 A | 6/1997 | Van Delden |
| 5,694,375 A | 12/1997 | Woodall |
| 5,719,497 A | 2/1998 | Veeser et al. |
| 5,731,996 A | 3/1998 | Gilbert |
| 5,764,061 A | 6/1998 | Asakawa et al. |
| 5,818,352 A | 10/1998 | McClure |
| 5,846,708 A | 12/1998 | Hollis et al. |
| 5,888,925 A | 3/1999 | Smith et al. |
| 5,907,420 A | 5/1999 | Chraplyvy et al. |
| 5,907,907 A | 6/1999 | Ohtomo et al. |
| 5,915,061 A | 6/1999 | Vanoli |
| 5,995,696 A | 11/1999 | Miyagi et al. |
| 6,042,249 A | 3/2000 | Spangenberg |
| 6,057,684 A | 5/2000 | Murakami et al. |
| 6,064,210 A | 5/2000 | Sinclair |
| 6,124,862 A | 9/2000 | Boyken et al. |
| 6,130,753 A | 10/2000 | Hopkins et al. |
| 6,144,204 A | 11/2000 | Sementchenko |
| 6,195,231 B1 | 2/2001 | Sedlmayr et al. |
| 6,215,303 B1 | 4/2001 | Weinstock et al. |
| 6,360,173 B1 | 3/2002 | Fullerton |
| 6,398,155 B1 | 6/2002 | Hepner et al. |
| 6,433,944 B1 | 8/2002 | Nagao et al. |
| 6,472,651 B1 | 10/2002 | Ukai |
| 6,472,869 B1 | 10/2002 | Upschulte et al. |
| 6,504,365 B2 | 1/2003 | Kitamura |
| 6,542,242 B1 | 4/2003 | Yost et al. |
| 6,621,578 B1 | 9/2003 | Mizoguchi |
| 6,636,146 B1 | 10/2003 | Wehoski |
| 6,686,696 B2 | 2/2004 | Mearini et al. |
| 6,690,162 B1 | 2/2004 | Schopohl et al. |
| 6,765,487 B1 | 7/2004 | Holmes et al. |
| 6,788,722 B1 | 9/2004 | Kennedy et al. |
| 6,809,829 B1 | 10/2004 | Takata et al. |
| 7,118,657 B2 | 10/2006 | Golovchenko et al. |
| 7,221,164 B1 | 5/2007 | Barringer |
| 7,277,161 B2 | 10/2007 | Claus |
| 7,305,869 B1 | 12/2007 | Berman et al. |
| 7,307,416 B2 | 12/2007 | Islam et al. |
| 7,342,399 B1 | 3/2008 | Wiegert |
| RE40,343 E | 5/2008 | Anderson |
| 7,400,142 B2 | 7/2008 | Greelish |
| 7,413,011 B1 | 8/2008 | Chee et al. |
| 7,427,525 B2 | 9/2008 | Santori et al. |
| 7,448,548 B1 | 11/2008 | Compton |
| 7,471,805 B2 | 12/2008 | Goldberg |
| 7,474,090 B2 | 1/2009 | Islam et al. |
| 7,543,780 B1 | 6/2009 | Marshall et al. |
| 7,546,000 B2 | 6/2009 | Spillane et al. |
| 7,570,050 B2 | 8/2009 | Sugiura |
| 7,608,820 B1 | 10/2009 | Berman et al. |
| 7,705,599 B2 | 4/2010 | Strack et al. |
| 7,805,030 B2 | 9/2010 | Bratkovski et al. |
| 7,868,702 B2 | 1/2011 | Ohnishi |
| 7,889,484 B2 | 2/2011 | Choi |
| 7,916,489 B2 | 3/2011 | Okuya |
| 7,932,718 B1 | 4/2011 | Wiegert |
| 7,983,812 B2 | 7/2011 | Potter |
| 8,022,693 B2 | 9/2011 | Meyersweissflog |
| 8,120,351 B2 | 2/2012 | Rettig et al. |
| 8,120,355 B1 | 2/2012 | Stetson |
| 8,124,296 B1 | 2/2012 | Fischel |
| 8,138,756 B2 | 3/2012 | Barclay et al. |
| 8,193,808 B2 | 6/2012 | Fu et al. |
| 8,294,306 B2 | 10/2012 | Kumar et al. |
| 8,310,251 B2 | 11/2012 | Orazem |
| 8,311,767 B1 | 11/2012 | Stetson |
| 8,334,690 B2 | 12/2012 | Kitching et al. |
| 8,415,640 B2 | 4/2013 | Babinec et al. |
| 8,471,137 B2 | 6/2013 | Adair et al. |
| 8,480,653 B2 | 7/2013 | Birchard et al. |
| 8,525,516 B2 | 9/2013 | Le Prado et al. |
| 8,547,090 B2 | 10/2013 | Lukin et al. |
| 8,574,536 B2 | 11/2013 | Boudou et al. |
| 8,575,929 B1 | 11/2013 | Wiegert |
| 8,686,377 B2 | 4/2014 | Twitchen et al. |
| 8,704,546 B2 | 4/2014 | Konstantinov |
| 8,758,509 B2 | 6/2014 | Twitchen et al. |
| 8,803,513 B2 | 8/2014 | Hosek et al. |
| 8,854,839 B2 | 10/2014 | Cheng et al. |
| 8,885,301 B1 | 11/2014 | Heidmann |
| 8,913,900 B2 | 12/2014 | Lukin et al. |
| 8,933,594 B2 | 1/2015 | Kurs |
| 8,947,080 B2 | 2/2015 | Lukin et al. |
| 8,963,488 B2 | 2/2015 | Campanella et al. |
| 9,103,873 B1 | 8/2015 | Martens et al. |
| 9,157,859 B2 | 10/2015 | Walsworth et al. |
| 9,245,551 B2 | 1/2016 | El Hallak et al. |
| 9,249,526 B2 | 2/2016 | Twitchen et al. |
| 9,270,387 B2 | 2/2016 | Wolfe et al. |
| 9,291,508 B1 | 3/2016 | Biedermann et al. |
| 9,317,811 B2 | 4/2016 | Scarsbrook |
| 9,369,182 B2 | 6/2016 | Kurs et al. |
| 9,442,205 B2 | 9/2016 | Geiser et al. |
| 9,541,610 B2 | 1/2017 | Kaup et al. |
| 9,551,763 B1 | 1/2017 | Hahn et al. |
| 9,557,391 B2 * | 1/2017 | Egan .................. G01R 33/032 |
| 9,570,793 B2 | 2/2017 | Borodulin |
| 9,590,601 B2 | 3/2017 | Krause et al. |
| 9,614,589 B1 | 4/2017 | Russo et al. |
| 9,645,223 B2 | 5/2017 | Megdal et al. |
| 9,680,338 B2 | 6/2017 | Malpas et al. |
| 9,689,679 B2 | 6/2017 | Budker et al. |
| 9,720,055 B1 | 8/2017 | Hahn et al. |
| 9,778,329 B2 | 10/2017 | Heidmann |
| 9,779,769 B2 | 10/2017 | Heidmann |
| 2002/0144093 A1 | 10/2002 | Inoue et al. |
| 2002/0167306 A1 | 11/2002 | Zalunardo et al. |
| 2003/0058346 A1 | 3/2003 | Bechtel et al. |
| 2003/0076229 A1 | 4/2003 | Blanpain et al. |
| 2003/0094942 A1 | 5/2003 | Friend et al. |

(56) References Cited

U.S. PATENT DOCUMENTS

| | | |
|---|---|---|
| 2003/0098455 A1 | 5/2003 | Amin et al. |
| 2003/0235136 A1 | 12/2003 | Akselrod et al. |
| 2004/0013180 A1 | 1/2004 | Giannakis et al. |
| 2004/0022179 A1 | 2/2004 | Giannakis et al. |
| 2004/0042150 A1 | 3/2004 | Swinbanks et al. |
| 2004/0081033 A1 | 4/2004 | Arieli et al. |
| 2004/0109328 A1 | 6/2004 | Dahl et al. |
| 2004/0247145 A1 | 12/2004 | Luo et al. |
| 2005/0031840 A1 | 2/2005 | Swift et al. |
| 2005/0068249 A1 | 3/2005 | Frederick Du Toit et al. |
| 2005/0099177 A1 | 5/2005 | Greelish |
| 2005/0112594 A1 | 5/2005 | Grossman |
| 2005/0126905 A1 | 6/2005 | Golovchenko et al. |
| 2005/0130601 A1 | 6/2005 | Palermo et al. |
| 2005/0134257 A1 | 6/2005 | Etherington et al. |
| 2005/0138330 A1 | 6/2005 | Owens et al. |
| 2005/0146327 A1 | 7/2005 | Jakab |
| 2006/0012385 A1 | 1/2006 | Tsao et al. |
| 2006/0054789 A1 | 3/2006 | Miyamoto et al. |
| 2006/0055584 A1 | 3/2006 | Waite et al. |
| 2006/0062084 A1 | 3/2006 | Drew |
| 2006/0071709 A1 | 4/2006 | Maloberti et al. |
| 2006/0245078 A1 | 11/2006 | Kawamura |
| 2006/0247847 A1 | 11/2006 | Carter et al. |
| 2006/0255801 A1 | 11/2006 | Ikeda |
| 2006/0291771 A1 | 12/2006 | Braunisch et al. |
| 2007/0004371 A1 | 1/2007 | Okanobu |
| 2007/0120563 A1 | 5/2007 | Kawabata et al. |
| 2007/0247147 A1 | 10/2007 | Xiang et al. |
| 2007/0273877 A1 | 11/2007 | Kawano et al. |
| 2008/0016677 A1 | 1/2008 | Creighton, IV |
| 2008/0048640 A1 | 2/2008 | Hull et al. |
| 2008/0078233 A1 | 4/2008 | Larson et al. |
| 2008/0089367 A1 | 4/2008 | Srinivasan et al. |
| 2008/0204004 A1 | 8/2008 | Anderson |
| 2008/0217516 A1 | 9/2008 | Suzuki et al. |
| 2008/0239265 A1 | 10/2008 | Den Boef |
| 2008/0253264 A1 | 10/2008 | Nagatomi et al. |
| 2008/0265895 A1 | 10/2008 | Strack et al. |
| 2008/0266050 A1 | 10/2008 | Crouse et al. |
| 2008/0279047 A1 | 11/2008 | An et al. |
| 2008/0299904 A1 | 12/2008 | Yi et al. |
| 2009/0001979 A1 | 1/2009 | Kawabata |
| 2009/0015262 A1 | 1/2009 | Strack et al. |
| 2009/0042592 A1 | 2/2009 | Cho et al. |
| 2009/0058697 A1 | 3/2009 | Aas et al. |
| 2009/0060790 A1 | 3/2009 | Okaguchi et al. |
| 2009/0079417 A1 | 3/2009 | Mort et al. |
| 2009/0079426 A1 | 3/2009 | Anderson |
| 2009/0132100 A1 | 5/2009 | Shibata |
| 2009/0157331 A1 | 6/2009 | Van Netten |
| 2009/0161264 A1 | 6/2009 | Meyersweissflog |
| 2009/0195244 A1 | 8/2009 | Mouget et al. |
| 2009/0222208 A1 | 9/2009 | Speck |
| 2009/0243616 A1 | 10/2009 | Loehken et al. |
| 2009/0277702 A1 | 11/2009 | Kanada et al. |
| 2009/0310650 A1 | 12/2009 | Chester et al. |
| 2010/0004802 A1 | 1/2010 | Bodin et al. |
| 2010/0015438 A1 | 1/2010 | Williams et al. |
| 2010/0015918 A1 | 1/2010 | Liu et al. |
| 2010/0045269 A1 | 2/2010 | Lafranchise et al. |
| 2010/0071904 A1 | 3/2010 | Burns et al. |
| 2010/0102809 A1 | 4/2010 | May |
| 2010/0102820 A1 | 4/2010 | Martinez et al. |
| 2010/0134922 A1 | 6/2010 | Yamada et al. |
| 2010/0157305 A1 | 6/2010 | Henderson |
| 2010/0188081 A1 | 7/2010 | Lammegger |
| 2010/0237149 A1 | 9/2010 | Olmstead |
| 2010/0271016 A1 | 10/2010 | Barclay et al. |
| 2010/0271032 A1 | 10/2010 | Helwig |
| 2010/0277121 A1 | 11/2010 | Hall et al. |
| 2010/0308813 A1 | 12/2010 | Lukin et al. |
| 2010/0315079 A1 | 12/2010 | Lukin et al. |
| 2010/0321117 A1 | 12/2010 | Gan |
| 2010/0326042 A1 | 12/2010 | McLean et al. |
| 2011/0034393 A1 | 2/2011 | Justen et al. |
| 2011/0059704 A1 | 3/2011 | Norimatsu et al. |
| 2011/0062957 A1 | 3/2011 | Fu et al. |
| 2011/0066379 A1 | 3/2011 | Mes |
| 2011/0120890 A1 | 5/2011 | MacPherson et al. |
| 2011/0127999 A1 | 6/2011 | Lott et al. |
| 2011/0165862 A1 | 7/2011 | Yu et al. |
| 2011/0175604 A1 | 7/2011 | Polzer et al. |
| 2011/0176563 A1 | 7/2011 | Friel et al. |
| 2011/0243267 A1 | 10/2011 | Won et al. |
| 2011/0270078 A1 | 11/2011 | Wagenaar et al. |
| 2011/0279120 A1 | 11/2011 | Sudow et al. |
| 2011/0315988 A1 | 12/2011 | Yu et al. |
| 2012/0016538 A1 | 1/2012 | Waite et al. |
| 2012/0019242 A1 | 1/2012 | Hollenberg et al. |
| 2012/0037803 A1 | 2/2012 | Strickland |
| 2012/0044014 A1 | 2/2012 | Stratakos et al. |
| 2012/0051996 A1 | 3/2012 | Scarsbrook et al. |
| 2012/0063505 A1 | 3/2012 | Okamura et al. |
| 2012/0087449 A1 | 4/2012 | Ling et al. |
| 2012/0089299 A1 | 4/2012 | Breed |
| 2012/0140219 A1 | 6/2012 | Cleary |
| 2012/0181020 A1 | 7/2012 | Barron et al. |
| 2012/0194068 A1 | 8/2012 | Cheng et al. |
| 2012/0203086 A1 | 8/2012 | Rorabaugh et al. |
| 2012/0232838 A1 | 9/2012 | Kemppi et al. |
| 2012/0235633 A1 | 9/2012 | Kesler et al. |
| 2012/0235634 A1 | 9/2012 | Hall et al. |
| 2012/0245885 A1 | 9/2012 | Kimishima |
| 2012/0257683 A1 | 10/2012 | Schwager et al. |
| 2012/0281843 A1 | 11/2012 | Christensen et al. |
| 2012/0326793 A1 | 12/2012 | Gan |
| 2013/0043863 A1 | 2/2013 | Ausserlechner et al. |
| 2013/0070252 A1 | 3/2013 | Feth |
| 2013/0093424 A1 | 4/2013 | Blank et al. |
| 2013/0107253 A1 | 5/2013 | Santori |
| 2013/0127518 A1 | 5/2013 | Nakao |
| 2013/0179074 A1 | 7/2013 | Haverinen |
| 2013/0215712 A1 | 8/2013 | Geiser et al. |
| 2013/0223805 A1 | 8/2013 | Ouyang et al. |
| 2013/0265042 A1 | 10/2013 | Kawabata et al. |
| 2013/0265782 A1 | 10/2013 | Barrena et al. |
| 2013/0270991 A1 | 10/2013 | Twitchen et al. |
| 2013/0279319 A1 | 10/2013 | Matozaki et al. |
| 2013/0292472 A1 | 11/2013 | Guha |
| 2014/0012505 A1 | 1/2014 | Smith et al. |
| 2014/0037932 A1 | 2/2014 | Twitchen et al. |
| 2014/0044208 A1 | 2/2014 | Woodsum |
| 2014/0061510 A1 | 3/2014 | Twitchen et al. |
| 2014/0070622 A1 | 3/2014 | Keeling et al. |
| 2014/0072008 A1 | 3/2014 | Faraon et al. |
| 2014/0077231 A1 | 3/2014 | Twitchen et al. |
| 2014/0081592 A1 | 3/2014 | Bellusci et al. |
| 2014/0104008 A1 | 4/2014 | Gan |
| 2014/0126334 A1 | 5/2014 | Megdal et al. |
| 2014/0139322 A1 | 5/2014 | Wang et al. |
| 2014/0153363 A1 | 6/2014 | Juhasz et al. |
| 2014/0154792 A1 | 6/2014 | Moynihan et al. |
| 2014/0159652 A1 | 6/2014 | Hall et al. |
| 2014/0166904 A1 | 6/2014 | Walsworth et al. |
| 2014/0167759 A1 | 6/2014 | Pines et al. |
| 2014/0168174 A1 | 6/2014 | Idzik et al. |
| 2014/0180627 A1 | 6/2014 | Naguib et al. |
| 2014/0191139 A1 | 7/2014 | Englund |
| 2014/0191752 A1 | 7/2014 | Walsworth et al. |
| 2014/0197831 A1 | 7/2014 | Walsworth |
| 2014/0198463 A1 | 7/2014 | Klein |
| 2014/0210473 A1 | 7/2014 | Campbell et al. |
| 2014/0215985 A1 | 8/2014 | Pollklas |
| 2014/0225606 A1 | 8/2014 | Endo et al. |
| 2014/0247094 A1 | 9/2014 | Englund et al. |
| 2014/0264723 A1 | 9/2014 | Liang et al. |
| 2014/0265555 A1 | 9/2014 | Hall et al. |
| 2014/0272119 A1 | 9/2014 | Kushalappa et al. |
| 2014/0273826 A1 | 9/2014 | Want et al. |
| 2014/0291490 A1 | 10/2014 | Hanson et al. |
| 2014/0297067 A1 | 10/2014 | Malay |
| 2014/0306707 A1 | 10/2014 | Walsworth et al. |
| 2014/0327439 A1 | 11/2014 | Cappellaro et al. |

(56) References Cited

U.S. PATENT DOCUMENTS

| | | |
|---|---|---|
| 2014/0335339 A1 | 11/2014 | Dhillon et al. |
| 2014/0340085 A1 | 11/2014 | Cappellaro et al. |
| 2014/0368191 A1 | 12/2014 | Goroshevskiy et al. |
| 2015/0001422 A1 | 1/2015 | Englund et al. |
| 2015/0009746 A1 | 1/2015 | Kucsko et al. |
| 2015/0015247 A1 | 1/2015 | Goodwill et al. |
| 2015/0018018 A1 | 1/2015 | Shen et al. |
| 2015/0022404 A1 | 1/2015 | Chen et al. |
| 2015/0048822 A1 | 2/2015 | Walsworth et al. |
| 2015/0054355 A1 | 2/2015 | Ben-Shalom et al. |
| 2015/0061590 A1 | 3/2015 | Widmer et al. |
| 2015/0061670 A1 | 3/2015 | Fordham et al. |
| 2015/0090033 A1 | 4/2015 | Budker et al. |
| 2015/0128431 A1 | 5/2015 | Kuo |
| 2015/0137793 A1 | 5/2015 | Englund et al. |
| 2015/0153151 A1 | 6/2015 | Kochanski |
| 2015/0192532 A1 | 7/2015 | Clevenson et al. |
| 2015/0192596 A1 | 7/2015 | Englund et al. |
| 2015/0225052 A1 | 8/2015 | Cordell |
| 2015/0235661 A1 | 8/2015 | Heidmann |
| 2015/0253355 A1 | 9/2015 | Grinolds et al. |
| 2015/0268373 A1 | 9/2015 | Meyer |
| 2015/0269957 A1 | 9/2015 | El Hallak et al. |
| 2015/0276897 A1 | 10/2015 | Leussler et al. |
| 2015/0288352 A1 | 10/2015 | Krause et al. |
| 2015/0299894 A1 | 10/2015 | Markham et al. |
| 2015/0303333 A1 | 10/2015 | Yu et al. |
| 2015/0314870 A1 | 11/2015 | Davies |
| 2015/0326030 A1 | 11/2015 | Malpas et al. |
| 2015/0326410 A1 | 11/2015 | Krause et al. |
| 2015/0354985 A1 | 12/2015 | Judkins et al. |
| 2015/0358026 A1 | 12/2015 | Gan |
| 2015/0374250 A1 | 12/2015 | Hatano et al. |
| 2015/0377865 A1 | 12/2015 | Acosta et al. |
| 2015/0377987 A1 | 12/2015 | Menon et al. |
| 2016/0018269 A1 | 1/2016 | Maurer et al. |
| 2016/0031339 A1 | 2/2016 | Geo |
| 2016/0036529 A1 | 2/2016 | Griffith et al. |
| 2016/0052789 A1 | 2/2016 | Gaathon et al. |
| 2016/0054402 A1 | 2/2016 | Meriles |
| 2016/0061914 A1 | 3/2016 | Jelezko |
| 2016/0071532 A9 | 3/2016 | Heidmann |
| 2016/0077167 A1 | 3/2016 | Heidmann |
| 2016/0097702 A1 | 4/2016 | Zhao et al. |
| 2016/0113507 A1 | 4/2016 | Reza et al. |
| 2016/0131723 A1 | 5/2016 | Nagasaka |
| 2016/0139048 A1 | 5/2016 | Heidmann |
| 2016/0146904 A1 | 5/2016 | Stetson, Jr. et al. |
| 2016/0161429 A1 | 6/2016 | Englund et al. |
| 2016/0161583 A1 | 6/2016 | Meriles et al. |
| 2016/0174867 A1 | 6/2016 | Hatano |
| 2016/0214714 A1 | 7/2016 | Sekelsky |
| 2016/0216304 A1 | 7/2016 | Sekelsky |
| 2016/0216340 A1 | 7/2016 | Egan et al. |
| 2016/0216341 A1 | 7/2016 | Boesch et al. |
| 2016/0221441 A1 | 8/2016 | Hall et al. |
| 2016/0223621 A1 | 8/2016 | Kaup et al. |
| 2016/0231394 A1 | 8/2016 | Manickam et al. |
| 2016/0266220 A1 | 9/2016 | Sushkov et al. |
| 2016/0282427 A1 | 9/2016 | Heidmann |
| 2016/0291191 A1 | 10/2016 | Fukushima et al. |
| 2016/0313408 A1 | 10/2016 | Hatano et al. |
| 2016/0348277 A1 | 12/2016 | Markham et al. |
| 2016/0356863 A1 | 12/2016 | Boesch et al. |
| 2017/0010214 A1 | 1/2017 | Osawa et al. |
| 2017/0010334 A1 | 1/2017 | Krause et al. |
| 2017/0010338 A1 | 1/2017 | Bayat et al. |
| 2017/0010594 A1 | 1/2017 | Kottapalli et al. |
| 2017/0023487 A1 | 1/2017 | Boesch |
| 2017/0030982 A1 | 2/2017 | Jeske et al. |
| 2017/0038314 A1 | 2/2017 | Suyama et al. |
| 2017/0038411 A1 | 2/2017 | Yacobi et al. |
| 2017/0068012 A1 | 3/2017 | Fisk |
| 2017/0074660 A1 | 3/2017 | Gann et al. |
| 2017/0075020 A1 | 3/2017 | Gann et al. |
| 2017/0075205 A1 | 3/2017 | Kriman et al. |
| 2017/0077665 A1 | 3/2017 | Liu et al. |
| 2017/0104426 A1 | 4/2017 | Mills |
| 2017/0138735 A1 | 5/2017 | Cappellaro et al. |
| 2017/0146615 A1 | 5/2017 | Wolf et al. |
| 2017/0199156 A1 | 7/2017 | Villani et al. |
| 2017/0205526 A1 | 7/2017 | Meyer |
| 2017/0207823 A1 | 7/2017 | Russo et al. |
| 2017/0211947 A1 | 7/2017 | Fisk |
| 2017/0212046 A1 | 7/2017 | Cammerata |
| 2017/0212177 A1 | 7/2017 | Coar et al. |
| 2017/0212178 A1 | 7/2017 | Hahn et al. |
| 2017/0212179 A1 | 7/2017 | Hahn et al. |
| 2017/0212180 A1 | 7/2017 | Hahn et al. |
| 2017/0212181 A1 | 7/2017 | Coar et al. |
| 2017/0212182 A1 | 7/2017 | Hahn et al. |
| 2017/0212183 A1 | 7/2017 | Egan et al. |
| 2017/0212184 A1 | 7/2017 | Coar et al. |
| 2017/0212185 A1 | 7/2017 | Hahn et al. |
| 2017/0212186 A1 | 7/2017 | Hahn et al. |
| 2017/0212187 A1 | 7/2017 | Hahn et al. |
| 2017/0212190 A1 | 7/2017 | Reynolds et al. |
| 2017/0212258 A1 | 7/2017 | Fisk |
| 2017/0261629 A1 | 9/2017 | Gunnarsson et al. |
| 2017/0343617 A1* | 11/2017 | Manickam ........... G01R 33/032 |
| 2017/0343619 A1* | 11/2017 | Manickam ........... G01R 33/032 |
| 2017/0343621 A1* | 11/2017 | Hahn ..................... G01N 21/64 |
| 2017/0343695 A1* | 11/2017 | Stetson ................. G01V 3/101 |
| 2018/0136291 A1 | 5/2018 | Pham et al. |

FOREIGN PATENT DOCUMENTS

| | | |
|---|---|---|
| DE | 69608006 T2 | 2/2001 |
| DE | 19600241 C2 | 8/2002 |
| DE | 10228536 A1 | 1/2003 |
| EP | 0 161 940 B1 | 12/1990 |
| EP | 0 718 642 | 6/1996 |
| EP | 0 726 458 | 8/1996 |
| EP | 1 505 627 | 2/2005 |
| EP | 1 685 597 | 8/2006 |
| EP | 1 990 313 | 11/2008 |
| EP | 2 163 392 | 3/2010 |
| EP | 2 495 166 A1 | 9/2012 |
| EP | 2 587 232 A1 | 5/2013 |
| EP | 2 705 179 | 3/2014 |
| EP | 2 707 523 | 3/2014 |
| EP | 2 745 360 | 6/2014 |
| EP | 2 769 417 | 8/2014 |
| EP | 2 790 031 | 10/2014 |
| EP | 2 837 930 A1 | 2/2015 |
| EP | 2 907 792 | 8/2015 |
| GB | 2 423 366 A | 8/2006 |
| GB | 2 433 737 | 7/2007 |
| GB | 2 482 596 | 2/2012 |
| GB | 2 483 767 | 3/2012 |
| GB | 2 486 794 | 6/2012 |
| GB | 2 490 589 | 11/2012 |
| GB | 2 491 936 | 12/2012 |
| GB | 2 493 236 | 1/2013 |
| GB | 2 495 632 A | 4/2013 |
| GB | 2 497 660 | 6/2013 |
| GB | 2 510 053 A | 7/2014 |
| GB | 2 515 226 | 12/2014 |
| GB | 2 522 309 | 7/2015 |
| GB | 2 526 639 | 12/2015 |
| JP | 3782147 B2 | 6/2006 |
| JP | 4800896 B2 | 10/2011 |
| JP | 2012-103171 | 5/2012 |
| JP | 2012-110489 | 6/2012 |
| JP | 2012-121748 | 6/2012 |
| JP | 2013-028497 | 2/2013 |
| JP | 5476206 B2 | 4/2014 |
| JP | 5522606 B2 | 6/2014 |
| JP | 5536056 B2 | 7/2014 |
| JP | 5601183 B2 | 10/2014 |
| JP | 2014-215985 | 11/2014 |
| JP | 2014-216596 | 11/2014 |
| JP | 2015-518562 A | 7/2015 |
| JP | 5764059 B2 | 8/2015 |

(56) References Cited

FOREIGN PATENT DOCUMENTS

| | | |
|---|---|---|
| JP | 2015-167176 | 9/2015 |
| JP | 2015-529328 | 10/2015 |
| JP | 5828036 B2 | 12/2015 |
| JP | 5831947 B2 | 12/2015 |
| WO | WO-87/04028 A1 | 7/1987 |
| WO | WO-88/04032 A1 | 6/1988 |
| WO | WO-95/33972 A1 | 12/1995 |
| WO | WO-2009/073736 | 6/2009 |
| WO | WO-2011/046403 A2 | 4/2011 |
| WO | WO-2011/153339 A1 | 12/2011 |
| WO | WO-2012/016977 A2 | 2/2012 |
| WO | WO-2012/084750 | 6/2012 |
| WO | WO-2013/027074 | 2/2013 |
| WO | WO-2013/059404 A1 | 4/2013 |
| WO | WO-2013/066446 A1 | 5/2013 |
| WO | WO-2013/066448 | 5/2013 |
| WO | WO-2013/093136 A1 | 6/2013 |
| WO | WO-2013/188732 A1 | 12/2013 |
| WO | WO-2013/190329 A1 | 12/2013 |
| WO | WO-2014/011286 A2 | 1/2014 |
| WO | WO-2014/099110 A2 | 6/2014 |
| WO | WO-2014/135544 A1 | 9/2014 |
| WO | WO-2014/135547 A1 | 9/2014 |
| WO | WO-2014/166883 A1 | 10/2014 |
| WO | WO-2014/210486 A1 | 12/2014 |
| WO | WO-2015/015172 A1 | 2/2015 |
| WO | WO-2015/142945 | 9/2015 |
| WO | WO-2015/157110 A1 | 10/2015 |
| WO | WO-2015/157290 A1 | 10/2015 |
| WO | WO-2015/158383 A1 | 10/2015 |
| WO | WO-2015/193156 A1 | 12/2015 |
| WO | WO-2016/075226 A1 | 5/2016 |
| WO | WO-2016/118756 A1 | 7/2016 |
| WO | WO-2016/118791 A1 | 7/2016 |
| WO | WO-2016/122965 A1 | 8/2016 |
| WO | WO-2016/122966 A1 | 8/2016 |
| WO | WO-2016/126435 A1 | 8/2016 |
| WO | WO-2016/126436 A1 | 8/2016 |
| WO | WO-2016/190909 A2 | 12/2016 |
| WO | WO-2017/007513 A1 | 1/2017 |
| WO | WO-2017/007514 A1 | 1/2017 |
| WO | WO-2017/014807 A1 | 1/2017 |
| WO | WO-2017/039747 A1 | 3/2017 |
| WO | WO-2017/095454 A1 | 6/2017 |
| WO | WO-2017/127079 A1 | 7/2017 |
| WO | WO-2017/127080 A1 | 7/2017 |
| WO | WO-2017/127081 A1 | 7/2017 |
| WO | WO-2017/127085 A1 | 7/2017 |
| WO | WO-2017/127090 A1 | 7/2017 |
| WO | WO-2017/127091 A1 | 7/2017 |
| WO | WO-2017/127093 A1 | 7/2017 |
| WO | WO-2017/127094 A1 | 7/2017 |
| WO | WO-2017/127095 A1 | 7/2017 |
| WO | WO-2017/127096 A1 | 7/2017 |
| WO | WO-2017/127097 A1 | 7/2017 |
| WO | WO-2017/127098 A1 | 7/2017 |

OTHER PUBLICATIONS

UK Office Action dated Jun. 8, 2018, from related application No. GB1617438.5, 3 pages.
U.S. Final Office Action dated Jul. 26, 2018 from related U.S. Appl. No. 15/003,177, 14 pages.
U.S. Non-Final Office Action dated Aug. 6, 2018 from related U.S. Appl. No. 15/376,244, 28 pages.
U.S. Non-Final Office Action dated Aug. 9, 2018 from related U.S. Appl. No. 15/003,309, 22 pages.
U.S. Non-Final Office Action dated Jul. 20, 2018 from related U.S. Appl. No. 15/350,303, 13 pages.
U.S. Non-Final Office Action dated Jul. 26, 2018 from related U.S. Appl. No. 15/380,419, 11 pages.
U.S. Non-Final Office Action dated Jul. 3, 2018 from related U.S. Appl. No. 15/003,396, 19 pages.
U.S. Notice of Allowance dated Jul. 18, 2018 from related U.S. Appl. No. 15/468,386, 12 pages.
U.S. Notice of Allowance dated Jul. 6, 2018 from related U.S. Appl. No. 15/672,953, 11 pages.
U.S. Notice of Allowance dated Jun. 27, 2018 from related U.S. Appl. No. 15/003,519, 21 pages.
U.S. Notice of Allowance dated May 15, 2018, from related U.S. Appl. No. 15/003,209, 7 pages.
U.S. Notice of Allowance dated May 16, 2018, from related U.S. Appl. No. 15/003,145, 8 pages.
U.S. Office Action dated Jun. 19, 2018, from related U.S. Appl. No. 15/450,504, 12 pages.
"'Diamond Sensors, Detectors, and Quantum Devices' in Patent Application Approval Process," Chemicals & Chemistry, pp. 1-6, (Feb. 28, 2014), 6 pages.
"Findings from University of Stuttgart in physics reported," Science Letter, (Jul. 7, 2009), 2 pages.
"New Findings on Nitrogen from Ecole Normale Superieure Summarized (Magnetic imaging with an ensemble of nitrogen vacancy-centers in diamond)," Physics Week, pp. 1-2, (Jul. 21, 2015), 2 pages.
"Patent Issued for Diamond Sensors, Detectors, and Quantum Devices (U.S. Pat. No. 9,249,526)," Journal of Engineering, pp. 1-5 (Feb. 15, 2016), 5 pages.
"Researchers Submit Patent Application, 'Diamond Sensors, Detectors, and Quantum Devices', for Approval," Chemicals & Chemistry, pp. 1-7, (Apr. 11, 2014), 7 pages.
Acosta et al., "Broadband magnetometry by infrared-absorption detection of nitrogen-vacancy ensembles in diamond," Appl. Phys. Letters 97: 174104 (Oct. 29, 2010), 4 pages.
Acosta et al., "Diamonds with a high density of nitrogen-vacancy centers for magnetometry applications," Physical Review B 80(115202): 1-15 (Sep. 9, 2009), 15 pages.
Acosta et al., "Nitrogen-vacancy centers: physics and applications," MRS Bulletin 38(2): 127-130 (Feb. 2013), 4 pages.
Acosta, "Optical Magnetometry with Nitrogen-Vacancy Centers in Diamond," University of California Berkeley, (Spring 2011), 118 pages.
Aiello et al., "Composite-pulse magnetometry with a solid-state quantum sensor," Nature Communications 4(1419): 1-6 (Jan. 29, 2013), 6 pages.
Alam, "Solid-state 13C magic angle spinning NMR spectroscopy characterization of particle size structural variations in synthetic nanodiamonds," Materials Chemistry and Physics 85(2-3): 310-315 (Jun. 15, 2004), 6 pages.
Albrecht et al., "Coupling of nitrogen vacancy centres in nanodiamonds by means of phonons," New Journal of Physics 15(083014): 1-26 (Aug. 6, 2013), 27 pages.
Appel et al., "Nanoscale microwave imaging with a single electron spin in diamond," New Journal of Physics 17(112001): 1-6 (Nov. 3, 2015), 7 pages.
Arai et al., "Fourier magnetic imaging with nanoscale resolution and compressed sensing speed-up using electronic spins in diamond," Nature Nanotechnology 10: 859-864 (Aug. 10, 2015), 7 pages.
Aslam et al., "Single spin optically detected magnetic resonance with 60-90 GHz (E-band) microwave resonators," Review of Scientific Instruments 86(064704): 1-8 (Jun. 22, 2015), 9 pages.
Awschalom et al., "Diamond age of spintronics," Scientific American 297: 84-91 (Oct. 2007), 8 pages.
Babamoradi et al., "Correlation between entanglement and spin density in nitrogen-vacancy center of diamond," European Physical Journal D 65: 597-603 (Dec. 1, 2011), 7 pages.
Babunts et al., "Diagnostics of NV defect structure orientation in diamond using optically detected magnetic resonance with a modulated magnetic field," Technical Physics Letters 41(6): 583-586 (Jun. 2015; first published online Jul. 14, 2015), 4 pages.
Babunts et al., "Temperature-scanned magnetic resonance and the evidence of two-way transfer of a nitrogen nuclear spin hyperfine interaction in coupled NV-N pairs in diamond," JETP Letters 95(8): 429-432 (Jun. 27, 2012), 4 pages.

(56) References Cited

OTHER PUBLICATIONS

Bagguley et al., "Zeeman effect of acceptor states in semiconducting diamond," Journal of the Physical Society of Japan 21(Supplement): 244-248 (1966), 7 pages.
Balasubramanian et al., "Nanoscale imaging magnetometry with diamond spins under ambient conditions," Nature 455: 648-651 (Oct. 2, 2008), 5 pages.
Balmer et al., "Chemical Vapour deposition synthetic diamond: materials technology and applications," J. of Physics: Condensed Matter 21(36): 1-51 (Aug. 19, 2009), 51 pages.
Baranov et al., "Enormously High Concentrations of Fluorescent Nitrogen-Vacancy Centers Fabricated by Sintering of Detonation Nanodiamonds," Small 7(11): 1533-1537 (Jun. 6, 2011; first published online Apr. 26, 2011), 5 pages.
Barfuss et al., "Strong mechanical driving of a single electron spin," Nature Physics 11: 820-824 (Aug. 3, 2015), 6 pages.
Barry et al., "Optical magnetic detection of single-neuron action potentials using quantum defects in diamond," as submitted to Quantum Physics on Feb. 2, 2016, 23 pages.
Bennett et al., "CVD Diamond for High Power Laser Applications," SPIE 8603, High-Power Laser Materials Processing: Lasers, Beam Delivery, Diagnostics, and Applications II, 860307 (Feb. 22, 2013), 10 pages.
Berman & Chernobrod, "Single-spin microscope with sub-nanoscale resolution based on optically detected magnetic resonance," SPIE 7608, Quantum Sensing and Nanophotonic Devices VII, 76080Y (Jan. 23, 2010), 4 pages.
Berman et al. "Measurement of single electron and nuclear spin states based on optically detected magnetic resonance," J. Physics: Conf. Series 38: 167-170 (2006), 5 pages.
Blakley et al., "Room-temperature magnetic gradiometry with fiber-coupled nitrogen-vacancy centers in diamond," Optics Letters 40(16): 3727-3730 (Aug. 5, 2015), 4 pages.
Bourgeois, et al., "Photoelectric detection of electron spin resonance of nitrogen-vacancy centres in diamond," Nature Communications 6(8577): 1-8 (Oct. 21, 2015), 8 pages.
Brenneis, et al. "Ultrafast electronic readout of diamond nitrogen-vacancy centres coupled to graphene." Nature nanotechnology 10.2 (2015): 135-139.
Bucher et al, "High Resolution Magnetic Resonance Spectroscopy Using Solid-State Spins", May 25, 2017, downloaded from https://arxiv.org/ (arXiv.org > quant-ph > arXiv:1705.08887) on May 25, 2017, pp. 1-24.
Budker & Kimball, "Optical Magnetometry," Cambridge Press, (2013), 11 pages.
Budker & Romalis, "Optical Magnetometry," Nature Physics 3: 227-243 (Apr. 2007), 8 pages.
Casanova, et al., "Effect of magnetic field on phosphorus centre in diamond," Physica Status Solidi A 186(2): 291-295 (Jul. 30, 2001), 6 pages.
Castelletto, et al., "Frontiers in diffraction unlimited optical methods for spin manipulation, magnetic field sensing and imaging using diamond nitrogen vacancy defects," Nanophotonics 1(2): 139-153 (Nov. 2012), 15 pages.
Chapman, et al., "Anomalous saturation effects due to optical spin depolarization in nitrogen-vacancy centers in diamond nanocrystals," Physical Review B 86(045204): 1-8 (Jul. 10, 2012), 8 pages.
Chavez, et al. "Detecting Arctic oil spills with NMR: a feasibility study." Near Surface Geophysics 13.4 (Feb. 2015): 409-416.
Chen et al., "Vector magnetic field sensing by a single nitrogen vacancy center in diamond," EPL 101(67003): 1-5 (Mar. 2013), 6 pages.
Chernobrod et al., "Improving the sensitivity of frequency modulation spectroscopy using nanomechanical cantilevers," Applied Physics Letters 85(17): 3896-3898 (Oct. 25, 2004), 3 pages.
Chernobrod et al., "Spin Microscope Based on Optically Detected Magnetic Resonance," Journal of Applied Physics 97(014903): 1-3, (2005; first published online Dec. 10, 2004), 4 pages.

Childress et al., "Coherent dynamics of coupled electron and nuclear spin qubits in diamond," Science 314(5797): 281-285 (Oct. 13, 2006), 6 pages.
Chipaux et al., "Magnetic imaging with an ensemble of nitrogen vacancy-centers in diamond," European Physical Journal D 69(166): 1-10 (Jul. 2, 2015), 10 pages.
Chipaux et al., "Nitrogen vacancies (NV) centers in diamond for magnetic sensors and quantum sensing," SPIE 9370, Quantum Sensing and Nanophotonic Devices XII, 93701V (Feb. 8, 2015), 6 pages.
Chipaux, et al., "Wide bandwidth instantaneous radio frequency spectrum analyzer based on nitrogen vacancy centers in diamond," Applied Physics Letters 107(233502): 1-5 (2015), 6 pages.
Clevenson et al., "Broadband magnetometry and temperature sensing with a light-trapping diamond waveguide," Nature Physics 11: 393-397 (May 2015; first published online Apr. 6, 2015), 6 pages.
Constable, "Geomagnetic Spectrum, Temporal." In Encyclopedia of Geomagnetism and Paleomagnetism, pp. 353-355, Springer: Dordrecht, Netherlands (2007), 3 pages.
Cooper et al., "Time-resolved magnetic sensing with electronic spins in diamond," Nature Communications 5:3141: 1-7 (Jan. 24, 2014), 7 pages.
Creedon et al., "Strong coupling between P1 diamond impurity centers and a three-dimensional lumped photonic microwave cavity," Physical Review B 91(140408R): 1-5 (Apr. 24, 2015), 5 pages.
Dale, et al. "Medical applications of diamond magnetometry: commercial viability." arXiv preprint arXiv:1705.01994 (May 8, 2017), pp. 1-7.
Davies, "Current problems in diamond: towards a quantitative understanding," Physica B 273-274: 15-13 (Dec. 15, 1999), 9 pages.
De Lange et al., "Single-Spin Magnetometry with Multipulse Sensing Sequences," Physical Review Letters 106(080802): 1-4 (Feb. 24, 2011), 4 pages.
Degen, "Scanning magnetic field microscope with a diamond single-spin sensor," Applied Physics Letters 92(243111): 1-3 (Jun. 17, 2008), 3 pages.
Delacroix et al., "Design, manufacturing, and performance analysis of mid-infrared achromatic half-wave plates with diamond subwavelength gratings," Applied Optics 51(24): 5897-5902 (Aug. 16, 2012), 6 pages.
Denatale et al., "Fabrication and characterization of diamond moth eye antireflective surfaces on Ge," J. of Applied Physics 71: 1388-1393 (Mar. 1992), 8 pages.
Dobrovitski et al., "Quantum Control over Single Spins in Diamond," Annual Review of Condensed Matter Physics 4: 23-50 (Apr. 2013), 30 pages.
Doherty et al., "The nitrogen-vacancy colour centre in diamond," Physics Reports 528: 1-45 (Jul. 1, 2013), 45 pages.
Doherty et al., "Theory of the ground-state spin of the NV- center in diamond," Physical Review B 85(205203): 1-21 (May 3, 2012), 21 pages.
Doi et al., "Pure negatively charged state of the NV center in n-type diamond," Physical Review B 93(081203): 1-6 (Feb. 3, 2016), 6 pages.
Drake et al., "Influence of magnetic field alignment and defect concentration on nitrogen-vacancy polarization in diamond," New Journal of Physics 18(013011): 1-8 (Jan. 2016; first published on Dec. 24, 2015), 9 pages.
Dreau et al., "Avoiding power broadening in optically detected magnetic resonance of single NV defects for enhanced dc magnetic field sensitivity," Physical Review B 84(195204): 1-8 (Nov. 23, 2011), 8 pages.
Dreau et al., "High-resolution spectroscopy of single NV defects coupled with nearby 13C nuclear spins in diamond," Physical Review B 85(134107): 1-7 (Apr. 20, 2012), 7 pages.
Dumeige et al., "Magnetometry with nitrogen-vacancy ensembles in diamond based on infrared absorption in a doubly resonant optical cavity," Physical Review B 87(155202): 1-9 (Apr. 8, 2013), 9 pages.
Epstein et al., "Anisotropic interactions of a single spin and dark-spin spectroscopy in diamond," Nature Physics 1:94-98 (Nov. 2005), 5 pages.
Fallah et al., "Multi-sensor approach in vessel magnetic wake imaging," Wave Motion 51(1): 60-76 (Jan. 2014), retrieved from

(56) References Cited

OTHER PUBLICATIONS http://www.sciencedirect.com/science/article/pii/S0165212513001133 (Aug. 21, 2016).
Fedotov et al., "High-resolution magnetic field imaging with a nitrogen-vacancy diamond sensor integrated with a photonic-crystal fiber," Optics Letters 41(3): 472-475 (Feb. 1, 2016; published Jan. 25, 2016), 4 pages.
Fedotov et al., "Photonic-crystal-fiber-coupled photoluminescence interrogation of nitrogen vacancies in diamond nanoparticles," Laser Physics Letters 9(2): 151-154 (Feb. 2012; first published online Dec. 2, 2011), 5 pages.
Feng & Wei, "A steady-state spectral method to fit microwave absorptions of NV centers in diamonds: application to sensitive magnetic field sensing," Measurement Science & Technology 25(105102): 1-6 (Oct. 2014; first published online Aug. 29, 2014), 7 pages.
Fologea, et al. "Detecting single stranded DNA with a solid state nanopore." Nano Letters 5.10 (Aug. 15, 2005): 1905-1909.
Freitas, et al., "Solid-State Nuclear Magnetic Resonance (NMR) Methods Applied to the Study of Carbon Materials," Chemistry and Physics of Carbon, vol. 31 (2012), 45 pages.
Gaebel, et al. "Room-temperature coherent coupling of single spins in diamond." Nature Physics 2.6 (May 28, 2006): 408-413.
GB Examination Report from United Kingdom application No. GB 1618202.4 dated Jan. 10, 2017.
Geiselmann et al., "Fast optical modulation of the fluorescence from a single nitrogen-vacancy centre," Nature Physics 9: 785-789 (Dec. 2013; first published online Oct. 13, 2013), 5 pages.
Gombert & Blasi, "The Moth-Eye Effect-From Fundamentals to Commercial Exploitation," Functional Properties of Bio-Inspired Surfaces: 79-102, (Nov. 2009), 26 pages.
Gong et al., "Generation of Nitrogen-Vacancy Center Pairs in Bulk Diamond by Molecular Nitrogen Implantation," Chinese Physics Letters 33(2)(026105): 1-4 (Feb. 2016), 5 pages.
Gould et al., "An imaging magnetometer for bio-sensing based on nitrogen-vacancy centers in diamond," SPIE 8933, Frontiers in Biological Detection: From Nanosensors to Systems VI, 89330L (Mar. 18, 2014), 8 pages.
Gould et al., "Room-temperature detection of a single 19 nm superparamagnetic nanoparticle with an imaging magnetometer," Applied Physics Letters 105(072406): 1-4 (Aug. 19, 2014), 5 pages.
Gruber et al., "Scanning confocal optical microscopy and magnetic resonance on single defect centers," Science 276(5321): 2012-2014 (Jun. 27, 1997), 4 pages.
Haeberle et al., "Nanoscale nuclear magnetic imaging with chemical contrast," Nature Nanotechnology 10: 125-128 (Feb. 2015; first published online Jan. 5, 2015), 4 pages.
Haihua et al., "Design of wideband anti-reflective sub wavelength nanostructures," Infrared and Laser Engineering 40(2): 267-270 (Feb. 2011), 4 pages.
Hall et al., "Sensing of Fluctuating Nanoscale Magnetic Fields Using Nitrogen-Vacancy Centers in Diamond," Physical Review Letters 103(220802): 1-4 (Nov. 25, 2009), 4 pages.
Hanson et al., "Coherent Dynamics of a Single Spin Interacting with an Adjustable Spin Bath," Science 320(5874): 352-355 (Apr. 18, 2008), 5 pages.
Hanson et al., "Polarization and Readout of Coupled Single Spins in Diamond," Physical Review Letters 97(087601): 1-4 (Aug. 23, 2006), 4 pages.
Hanson et al., "Room-temperature manipulation and decoherence of a single spin in diamond," Physical Review 74(161203): 1-4 (Oct. 26, 2006), 4 pages.
Hanzawa et al., "Zeeman effect on the zero-phonon line of the NV center in synthetic diamond," Physica B 184(1-4): 137-140 (Feb. 1993), 4 pages.
Heerema, et al. "Graphene nanodevices for DNA sequencing." Nature nanotechnology 11.2 (Feb. 3, 2016): 127-136.
Hegyi & Yablonovitch, "Molecular imaging by optically detected electron spin resonance of nitrogen-vacancies in nanodiamonds," Nano Letters 13(3): 1173-1178 (Mar. 2013; first published online Feb. 6, 2013), 6 pages.
Hegyi & Yablonovitch, "Nanodiamond molecular imaging with enhanced contrast and expanded field of view," Journal of Biomedical Optics 19(1)(011015): 1-8 (Jan. 2014), 9 pages.
Hilser et al., "All-optical control of the spin state in the NV- center in diamond," Physical Review B 86(125204): 1-8 (Sep. 14, 2012), 8 pages.
Hobbs, "Study of the Environmental and Optical Durability of AR Microstructures in Sapphire, ALON, and Diamond," SPIE 7302, Window and Dome Technologies and Materials XI, 73020J (Apr. 27, 2009), 14 pages.
Huebener et al., "ODMR of NV centers in nano-diamonds covered with N@C60," Physica Status Solidi B 245(10): 2013-2017 (Oct. 2008; first published online Sep. 8, 2008), 5 pages.
Huxter et al., "Vibrational and electronic dynamics of nitrogen-vacancy centres in diamond revealed by two-dimensional ultrafast spectroscopy," Nature Physics 9: 744-749 (Sep. 29, 2013), 6 pages.
International Search Report and Written Opinion from related PCT application PCT/US2017/035315 dated Aug. 24, 2017, 7 pages.
International Search Report and Written Opinion of the International Searching Authority dated Apr. 1, 2016 from related PCT application PCT/US2016/014384, 12 pages.
International Search Report and Written Opinion of the International Searching Authority dated Apr. 11, 2016 from related PCT application PCT/US2016/014376, 12 pages.
International Search Report and Written Opinion of the International Searching Authority dated Apr. 11, 2016 from related PCT application PCT/US2016/014388, 14 pages.
International Search Report and Written Opinion of the International Searching Authority dated Apr. 11, 2016 from related PCT application PCT/US2016/014395, 15 pages.
International Search Report and Written Opinion of the International Searching Authority dated Apr. 4, 2017 from related PCT application PCT/US16/68366, 9 pages.
International Search Report and Written Opinion of the International Searching Authority dated Feb. 15, 2017 from related PCT application PCT/US2016/014390, 20 pages.
International Search Report and Written opinion of the International Searching Authority dated Jul. 12, 2016, from related PCT application PCT/US2016/014287, 14 pages.
International Search Report and Written Opinion of the International Searching Authority dated Jul. 16, 2015, from related PCT application PCT/US2015/24723, 8 pages.
International Search Report and Written Opinion of the International Searching Authority dated Jul. 6, 2015, from related PCT application PCT/US2015/021093, 9 pages.
International Search Report and Written Opinion of the International Searching Authority dated Jul. 8, 2015, from related PCT application PCT/US2015/024265, 11 pages.
International Search Report and Written Opinion of the International Searching Authority dated Jun. 1, 2017, from related PCT application PCT/US17/21811, 9 pages.
International Search Report and Written Opinion of the International Searching Authority dated Jun. 1, 2017, in related PCT application PCT/US17/22279, 20 pages.
International Search Report and Written Opinion of the International Searching Authority dated Jun. 10, 2016 from related PCT application PCT/US2016/014290, 11 pages.
International Search Report and Written Opinion of the International Searching Authority dated Jun. 15, 2017, from related PCT application PCT/US2017/024175, 10 pages.
International Search Report and Written Opinion of the International Searching Authority dated Jun. 2, 2016, from related PCT application PCT/US2016/014386, 14 pages.
International Search Report and Written Opinion of the International Searching Authority dated Jun. 2, 2016, from related PCT application PCT/US2016/014387, 13 pages.
International Search Report and Written Opinion of the International Searching Authority dated Jun. 6, 2016, from related PCT application PCT/US2016/014291, 13 pages.

(56) References Cited

OTHER PUBLICATIONS

International Search Report and Written Opinion of the International Searching Authority dated Jun. 9, 2016 from related PCT application PCT/US2016/014333, 16 pages.
International Search Report and Written Opinion of the International Searching Authority dated Jun. 9, 2017, from related patent application PCT/US2017/024181, 13 pages.
International Search Report and Written Opinion of the International Searching Authority dated Jun. 9, 2017, from related PCT application PCT/US2017/024179, 9 pages.
International Search Report and Written Opinion of the International Searching Authority dated Mar. 13, 2017 from related PCT application PCT/US2016/68320, 10 pages.
International Search Report and Written Opinion of the International Searching Authority dated Mar. 24, 2016 from related PCT application PCT/US2016/014336, 17 pages.
International Search Report and Written Opinion of the International Searching Authority dated Mar. 24, 2016 from related PCT application PCT/US2016/014297, 15 pages.
International Search Report and Written Opinion of the International Searching Authority dated Mar. 24, 2016 from related PCT application PCT/US2016/014392, 8 pages.
International Search Report and Written Opinion of the International Searching Authority dated Mar. 24, 2016 from related PCT application PCT/US2016/014403, 10 pages.
International Search Report and Written Opinion of the International Searching Authority dated Mar. 25, 2016, from related PCT application PCT/US2016/014363, 8 pages.
International Search Report and Written Opinion of the International Searching Authority dated Mar. 25, 2016, from related PCT application PCT/US2016/014389, 19 pages.
International Search Report and Written Opinion of the International Searching Authority dated Mar. 27, 2017 from related PCT application PCT/US16/68344, 16 pages.
International Search Report and Written Opinion of the International Searching Authority dated Mar. 28, 2016, from related PCT application PCT/US2016/014380, 9 pages.
International Search Report and Written Opinion of the International Searching Authority dated Mar. 28, 2016, from related PCT application PCT/US2016/014394, 17 pages.
International Search Report and Written Opinion of the International Searching Authority dated Mar. 29, 2016 from related PCT application PCT/US2016/014325, 11 pages.
International Search Report and Written Opinion of the International Searching Authority dated Mar. 29, 2016 from related PCT application PCT/US2016/014330, 8 pages.
International Search Report and Written Opinion of the International Searching Authority dated Mar. 29, 2016 from related PCT application PCT/US2016/014328, 7 pages.
International Search Report and Written Opinion of the International Searching Authority dated Mar. 29, 2016 from related PCT application PCT/US2016/014385, 11 pages.
International Search Report and Written Opinion of the International Searching Authority dated Mar. 30, 2016 from related PCT application PCT/US2016/014298, 14 pages.
International Search Report and Written Opinion of the International Searching Authority dated Mar. 31, 2016 from related PCT application PCT/US2016/014375, 11 pages.
International Search Report and Written Opinion of the International Searching Authority dated Mar. 31, 2016 from related PCT application PCT/US2016/014396, 11 pages.
International Search Report and Written Opinion of the International Searching Authority dated Mar. 31, 2017 from related PCT application PCT/US2016/066566, 11 pages.
International Search Report and Written Opinion of the International Searching Authority dated May 10, 2017 from related PCT application PCT/US17/19411, 8 pages.
International Search Report and Written Opinion of the International Searching Authority dated May 18, 2017, from related PCT application PCT/US2017/021593, 10 pages.
International Search Report and Written Opinion of the International Searching Authority dated May 19, 2017, from related PCT application PCT/US17/18099, 16 pages.
International Search Report and Written Opinion of the International Searching Authority dated May 26, 2016, from related PCT application PCT/US2016/014331, 15 pages.
International Search Report and Written Opinion of the International Searching Authority dated May 3, 2017 from related PCT application PCT/US2017/018701, 8 pages.
International Search Report and Written Opinion of the International Searching Authority dated May 4, 2017 from related PCT application PCT/US2017/018709, 8 pages.
International Search Report and Written Opinion of the International Searching Authority dated May 8, 2017 from related PCT application PCT/US2017/17321, 17 pages.
International Search Report and Written Opinion of the International Searching Authority dated Sep. 13, 2016, from related PCT application PCT/US16/14377, 11 pages.
International Search Report and Written Opinion of the International Searching Authority dated Jul. 14, 2017, from related PCT application PCT/US2017/022118, 13 pages.
International Search Report and Written Opinion of the International Searching Authority dated Jul. 17, 2017, from related PCT application PCT/US2017/024177, 11 pages.
International Search Report and Written Opinion of the International Searching Authority dated Jul. 18, 2017, from related PCT application PCT/US2017/024167, 11 pages.
International Search Report and Written Opinion of the International Searching Authority dated Jul. 18, 2017, from related PCT application PCT/US2017/024173, 13 pages.
International Search Report and Written Opinion of the International Searching Authority dated Jul. 19, 2017, from related PCT application PCT/US2017/024171, 12 pages.
International Search Report and Written Opinion of the International Searching Authority dated Jun. 15, 2017, from related PCT application PCT/US2017/024182, 21 pages.
International Search Report and Written Opinion of the International Searching Authority dated Jun. 22, 2017, in related PCT application PCT/US2017/024180, 10 pages.
International Search Report and Written Opinion of the International Searching Authority dated Jun. 5, 2017, from related PCT application PCT/US2017/024169, 11 pages.
International Search Report and Written Opinion of the International Searching Authority dated Jun. 5, 2017, from related PCT application PCT/US2017/024174, 8 pages.
International Search Report and Written Opinion of the International Searching Authority dated Jun. 5, 2017, in related PCT application PCT/US2017/024168, 7 pages.
International Search Report and Written Opinion of the International Searching Authority dated Jun. 6, 2017, from related PCT application PCT/2017/024165, 9 pages.
International Search Report and Written Opinion of the International Searching Authority dated Jun. 6, 2017, from related PCT application PCT/US2017/024172, 9 pages.
Ivady et al., "Pressure and temperature dependence of the zero-field splitting in the ground state of NV centers in diamond: A first-principles study," Physical Review B 90(235205): 1-8 (Dec. 2014), 8 pages.
Jarmola et al., "Temperature- and Magnetic-Field-Dependent Longitudinal Spin Relaxation in Nitrogen-Vacancy Ensembles in Diamond," Physical Review Letters 108 (197601): 1-5 (May 2012), 5 pages.
Jensen et al., "Light narrowing of magnetic resonances in ensembles of nitrogen-vacancy centers in diamond," Physical Review B 87(014115): 1-10 (Jan. 2013), 10 pages.
Kailath, "Linear Systems," Prentice Hall, (1979), 6 pages.
Karlsson et al., "Diamond micro-optics: microlenses and antireflection structures surfaces for the infrared spectral region," Optics Express 11(5): 502-507 (Mar. 10, 2003), 6 pages.
Keyser "Enhancing nanopore sensing with DNA nanotechnology." Nature nanotechnology 11.2 (Feb. 2016): 106-108.
Khan & Hemmer, "Noise limitation in nano-scale imaging," Proceedings of SPIE vol. 5842: 302-305, (Dec. 2005), 7 pages.

(56) References Cited

OTHER PUBLICATIONS

Kim et al., "Electron spin resonance shift and linewidth broadening of nitrogen-vacancy centers in diamond as a function of electron irradiation dose," Applied Physics Letters 101(082410): 1-5 (Aug. 2012), 6 pages.

Kim et al., "Jahn-Teller Splitting and Zeeman Effect of Acceptors in Diamond," Physica B 273-274: 647-627 (Jul. 1999), 4 pages.

Kim et al., "Magnetospectroscopy of acceptors in 'blue' diamonds," Physica B 302-301: 88-100 (Aug. 2001), 13 pages.

Kim et al., "Zeeman effect of electronic Raman lines of accepters in elemental semiconductors: Boron in blue diamond," Physical Review B 62(12): 8038-8052 (Sep. 2000), 15 pages.

King et al., "Optical polarization of 13C nuclei in diamond through nitrogen vacancy centers," Physical Review B 81(073201): 1-4 (Feb. 2010), 4 pages.

Kok et al., "Materials Science: Qubits in the pink," Nature 444(2): 49 (Nov. 2006), 1 page.

Konenko et al., "Formation of antireflective surface structures on diamond films by laser patterning," Applied Physics A 68:99-102 (Jan. 1999), 4 pages.

Kraus et al., "Magnetic field and temperature sensing with atomic-scale spin defects in silicon carbide," Scientific Reports 4(5303): 1-8 (Jul. 2014), 8 pages.

Lai et al., "Influence of a static magnetic field on the photoluminescence of an ensemble of nitrogen-vacancy color centers in a diamond single-crystal," Applied Physics Letters 95, (Sep. 2009), 4 pages.

Lai et al., "Optically detected magnetic resonance of a single Nitrogen-Vacancy electronic spin in diamond nanocrystals," CLEO/EQEC, (Jun. 14-19, 2009), 1 page.

Laraoui et al., "Nitrogen-vacancy assisted magnetometry of paramagnetic centers in an individual diamond nanocrystal," Nano Letters 12: 3477-3482 (Jul. 2012), 6 pages.

Lazariev et al., "A nitrogen-vacancy spin based molecular structure microscope using multiplexed projection reconstruction," Scientific Reports 5(14130): 1-8 (Sep. 2015), 8 pages.

Le Sage et al., "Efficient photon detection from color centers in a diamond optical waveguide," Phys. Rev. B 85: 121202(R), pp. 121202-1-121202-4, (Mar. 23, 2012), 4 pages.

Lee et al., "Vector magnetometry based on S=3/2 electronic spins," Physical Review B 92 (115201): 1-7 (Sep. 2015), 7 pages.

Lesik et al., "Preferential orientation of NV defects in CVD diamond films grown on (113)-oriented substrates," Diamond and Related Materials 56: 47-53 (Jun. 2015), 7 pages.

Levchenko et al., "Inhomogeneous broadening of optically detected magnetic resonance of the ensembles of nitrogen-vacancy centers in diamond by interstitial carbon atoms," Applied Physics Letters 106, (Mar. 2015; published online Mar. 9, 2015), 6 pages.

Lindsay "The promises and challenges of solid-state sequencing." Nature nanotechnology 11.2 (Feb. 2016): 109-111.

Liu et al., "Electron spin studies of nitrogen vacancy centers in nanodiamonds," Acta Physica Sinica 62(16) 164208: 1-5 (Aug. 2013), 5 pages.

Liu et al., "Fiber-integrated diamond-based magnetometer," Applied Physics Letters 103(143105): 1-4 (Sep. 2013), 5 pages.

MacLaurin et al., "Nanoscale magnetometry through quantum control of nitrogen-vacancy centres in rotationally diffusing nanodiamonds," New Journal of Physics 15, (Jan. 2013), 16 pages.

MacQuarie et al., "Mechanical spin control of nitrogen-vacancy centers in diamond," Retrieved from http://www.arxiv.org/pdf/1306.6356.pdf, pp. 1-8, (Jun. 2013), 8 pages.

Macs et al., "Diamond as a magnetic field calibration probe," Journal of Physics D: Applied Physics 37, (Apr. 2004; published Mar. 17, 2004), 6 pages.

Maletinsky et al., "A robust scanning diamond sensor for nanoscale imaging with single nitrogen-vacancy centres," Nature Nanotechnology 7: 320-324, (May 2012; published Apr. 15, 2012), 5 pages.

Mamin et al., "Multipulse Double-Quantum Magnetometry with Near-Surface Nitrogen-Vacancy Centers," Physical Review Letters 13(030803): 1-5 (Jul. 2014), 5 pages.

Mamin et al., "Nanoscale Nuclear Magnetic Resonance with a Nitrogen-Vacancy Spin Sensor," Science 339, (Feb. 2013), 5 pages.

Manson et al., "GR transitions in diamond: magnetic field measurements," Journal of Physics C Solid St. Phys 13: L1005-L1009, (Nov. 1980), 6 pages.

Massachusetts Institute of Technology, "Wide-Field Imaging Using Nitrogen Vacancies," in Patent Application Approval Process, Physics Week: 1-5, (Jan. 20, 2015), 5 pages.

Matlashov, et al. "SQUIDs for magnetic resonance imaging at ultra-low magnetic field." PIERS online 5.5 (2009): 466-470.

Matlashov, et al. "SQUIDs vs. induction coils for ultra-low field nuclear magnetic resonance: experimental and simulation comparison." IEEE Transactions on Applied Superconductivity 21.3 (Jan. 1, 2012): 465-468.

Matsuda et al., "Development of a plastic diamond anvil cell for high pressure magneto-photoluminescence in pulsed high magnetic fields," International Journal of Modern Physics B 18(27-29), (Nov. 2004), 7 pages.

Maze et al., "Nanoscale magnetic sensing using spin qubits in diamond," Proc. SPIE 7225, Advanced Optical Concepts in Quantum Computing, Memory, and Communication II, 722509 (Feb. 2, 2009) 8 pages.

Maze et al., "Nanoscale magnetic sensing with an individual electronic spin in diamond," Nature Physics 455: 644-647 (Oct. 2, 2008), 5 pages.

Meijer et al., "Generation of single color centers by focused nitrogen implantation," Applied Physics Letters 87(261909): 1-3 (Dec. 2005), 4 pages.

Michaelovich et al., "Polarization Dependencies of the Nitrogen-Vacancy Center." Undergraduate Project Report, Ben-Gurion University, Aug. 2015, pp. 1-9.

Millot et al., "High-field Zeeman and Paschen-Back effects at high pressure in oriented ruby," Physical Review B 78 (155125): 1-7 (Oct. 2008), 7 pages.

Moessle, et al. "SQUID-detected magnetic resonance imaging in microtesla fields." Annu. Rev. Biomed. Eng. 9 (May 23, 2008): 389-413.

Moriyama et al., "Importance of electron-electron interactions and Zeeman splitting in single-wall carbon nanotube quantum dots," Physica E 26: 473-476 (Feb. 2005), 4 pages.

Mrozek et al., "Circularly polarized microwaves for magnetic resonance study in the GHz range: Application to nitrogen-vacancy in diamonds," Applied Physics Letters, pp. 1-4 (Jul. 2015), 4 pages.

Nagl et al., "Improving surface and defect center chemistry of fluorescent nanodiamonds for imaging purposes-a review," Analytical and Bioanalaytical Chemistry 407: 7521-7536 (Oct. 2015; published online Jul. 29, 2015), 16 pages.

Neumann et al., "Excited-state spectroscopy of single NV defects in diamond using optically detected magnetic resonance," New Journal of Physics 11(013017): 1-10, (Jan. 2009), 11 pages.

Nizovtsev & Kilin, "Optically Detected Magnetic Resonance Spectra of the 14NV-13C Spin Systems in Diamond: Analytical Theory and Experiment," Doklady of the National Academy of Sciences of Belarus, (2013), 27 pages with English machine translation.

Nizovtsev et al., "Modeling fluorescence of single nitrogen-vacancy defect centers in diamond," Physica B—Condensed Matter, 608-611 (Dec. 2001), 4 pages.

Nizovtsev et al., "Theoretical study of hyperfine interactions and optically detected magnetic resonance spectra by simulation of the C-291(NV)H-(172) diamond cluster hosting nitrogen-vacancy center," New Journal of Physics 16(083014): 1-21 (Aug. 2014), 22 pages.

Nobauer et al., "Smooth optimal quantum control for robust solid state spin magnetometry," Retrieved from http://www.arxiv.org/abs/1412.5051, pp. 1-12, (Dec. 2014), 12 pages.

Nowodzinski et al., "Nitrogen-Vacancy centers in diamond for current imaging at the redistributive layer level of Integrated Circuits," Microelectronics Reliability 55: 1549-1553 (Aug. 2015), 5 pages.

Nusran et al., "Optimizing phase-estimation algorithms for diamond spin magnetometry," Physical Review B 90(024422): 1-12 (Jul. 2014), 12 pages.

(56) References Cited

OTHER PUBLICATIONS

Ohashi et al., "Negatively Charged Nitrogen-Vacancy Centers in a 5 nm Thin 12C Diamond Film," Nano Letters 13: 4733-4738 (Oct. 2013), 6 pages.
Pelliccione, et al., Two-dimensional nanoscale imaging of gadolinium spins via scanning probe relaxometry with a single spin in diamond, Phys. Rev. Applied 2.5, (Sep. 8, 2014): 054014 pp. 1-17.
Plakhotnik et al., "Super-Paramagnetic Particles Chemically Bound to Luminescent Diamond : Single Nanocrystals Probed with Optically Detected Magnetic Resonance," Journal of Physical Chemistry C 119: 20119-20124 (Aug. 2015), 6 pages.
Polatomic. "AN/ASQ-233A Digital Magnetic Anomaly Detective Set." Retrieved May 9, 2016, from http://polatomic.com/images/DMAD_Data_Sheet_09-2009.pdf (2009), 1 page.
Poole, "What is GMSK Modulation—Gaussian Minimum Shift Keying." Radio-Electronics, retrieved from https://web.archive.org/web/20150403045840/http://www.radio-electronics.com/info/rf-technology-design/pm-phase-modulation/what-is-gmsk-gaussian-minimum-shift-keyingtutorial.php (Apr. 3, 2015), 4 pages.
Qiu et al., "Low-field NMR Measurement Procedure when SQUID Detection is Used," IEEE/CSC & ESAS European Superconductivity News Forum, No. 5, Jul. 2008.
Qiu, et al. "SQUID-detected NMR in Earth's magnetic field." Journal of Physics: Conference Series. vol. 97. No. 1. IOP Publishing, Mar. 2008, pp. 1-7.
Rabeau et al., "Implantation of labelled single nitrogen vacancy centers in diamond using 15N," Applied Physics Letters 88, (Jan. 2006), 4 pages.
Ramsey, et al., "Phase Shifts in the Molecular Beam Method of Separated Oscillating Fields", Physical Review, vol. 84, No. 3, Nov. 1, 1951, pp. 506-507.
Ranjbar et al., "Many-electron states of nitrogen-vacancy centers in diamond and spin density calculations," Physical Review B 84(165212): 1-6 (Oct. 2011), 6 pages.
Reynhardt, "Spin-lattice relaxation of spin-1/2 nuclei in solids containing diluted paramagnetic impurity centers. I. Zeeman polarization of nuclear spin system," Concepts in Magnetic Resonance Part A, pp. 20-35, (Sep. 2003), 16 pages.
Rogers et al., "Singlet levels of the NV(-) centre in diamond," New Journal of Physics 17, (Jan. 2015), 13 pages.
Rondin et al., "Magnetometry with nitrogen-vacancy defects in diamond," Reports on Progress in Physics 77(056503) 1-26 (May 2014), 27 pages.
Rondin et al., "Magnetometry with nitrogen-vacancy defects in diamond." May 22, 2014 (May 22, 2014), pp. 1 [online] http://arxiv.org/pdf/1311.5214.pdf, 29 pages.
Rondin et al., "Nanoscale magnetic field mapping with a single spin scanning probe magnetometer," Applied Physics Letters 100, (Apr. 2012), 5 pages.
Sarkar et al., "Magnetic properties of graphite oxide and reduced graphene oxide," Physica E 64: 78-82 (Nov. 2014), 5 pages.
Scheuer et al., "Accelerated 2D magnetic resonance spectroscopy of single spins using matrix completion," Scientific Reports 5(17728): 1-8 (Dec. 2015), 8 pages.
Schirhagl et al., "Nitrogen-vacancy centers in diamond: Nanoscale sensors for physics and biology," Annual Review of Physical Chemistry 65: 83-105 (Jan. 2014), 26 pages.
Schoenfeld & Harneit, "Real time magnetic field sensing and imaging using a single spin in diamond," Physical Review Letters 106(030802): 1-4 (Jan. 2011), 4 pages.
Sedov et al., "Si-doped nano- and microcrystalline diamond films with controlled bright photoluminescence of silicon-vacancy color centers," Diamond and Related Materials 56: 23-28 (Jun. 2015; available online Apr. 18, 2015), 6 pages.
Shames et al., "Magnetic resonance tracking of fluorescent nanodiamond fabrication," Journal of Physics D: Applied Physics 48(155302): 1-13 (Apr. 2015; published Mar. 20, 2015), 14 pages.

Shao et al., "Diamond Color Center Based FM Microwave Demodulator," in Conference on Lasers and Electro-Optics, OSA Technical Digest (online) (Optical Society of America), paper JTh2A.136, (Jun. 5-10, 2016), 2 pages.
Sheinker et al., "Localization in 3-D Using Beacons of Low Frequency Magnetic Field." IEEE Transactions on Instrumentation and Measurement 62(12): 3194-3201 (Dec. 2013), 8 pages.
Simanovskaia et al., "Sidebands in optically detected magnetic resonance signals of nitrogen vacancy centers in diamond," Physical Review B 87(224106): 1-11 (Jun. 2013), 11 pages.
Sotoma et al., "Effective production of fluorescent nanodiamonds containing negatively-charged nitrogen-vacancy centers by ion irradiation," Diamond and Related Materials 49: 33-38 (Oct. 2014), 6 pages.
Soykal et al., "Quantum metrology with a single spin-3/2 defect in silicon carbide," Mesoscale and Nanoscale Physics (May 24, 2016), retrieved from https://arxiv.org/abs/1605.07628 (Sep. 22, 2016), 9 pages.
Steiner et al., "Universal enhancement of the optical readout fidelity of single electron spins at nitrogen-vacancy centers in diamond," Physical Review B 81(035205): 1-6 (Jan. 2010), 6 pages.
Steinert et al., "High-sensitivity magnetic imaging using an array of spins in diamond," Rev. Sci. Inst. 81(043705): 1-5 (Apr. 23, 2010), 5 pages.
Steinert et al., "Magnetic spin imaging under ambient conditions with sub-cellular resolution." Nature Comms 4:1607 (Mar. 19, 2013).
Stepanov et al., "High-frequency and high-field optically detected magnetic resonance of nitrogen-vacancy centers in diamond," Applied Physics Letters 106, (Feb. 2015), 5 pages.
Sternschulte et al., "Uniaxial stress and Zeeman splitting of the 1.681 eV optical center in a homoepitaxial CVD diamond film," Diamond and Related Materials 4: 1189-1192 (Sep. 1995), 4 pages.
Storteboom et al., "Lifetime investigation of single nitrogen vacancy centres in nanodiamonds," Optics Express 23(9): 11327-11333 (May 4, 2015; published Apr. 22, 2015), 7 pages.
Sushkov, et al. "All-optical sensing of a single-molecule electron spin." Nano letters 14.11 (Nov. 7, 2013): 6443-6448.
Tahara et al., "Quantifying selective alignment of ensemble nitrogen-vacancy centers in (111) diamond," Applied Physics Letters 107:193110 (Nov. 2015; published online Nov. 13, 2015), 5 pages.
Taylor et al., "High-sensitivity diamond magnetometer with nanoscale resolution," Nature Physics 4: 810-816 (Oct. 2008), 7 pages.
Teale, "Magnetometry with Ensembles of Nitrogen Vacancy Centers in Bulk Diamond," Master's Thesis, Massachusetts Institute of Technology Department of Electrical Engineering and Computer Science (Sep. 2015), 57 pages.
Terblanche et al., "13C spin-lattice relaxation in natural diamond: Zeeman relaxation at 4.7 T and 300 K due to fixed paramagnetic nitrogen defects," Solid State Nuclear Magnetic Resonance 20: 1-22 (Aug. 2001), 22 pages.
Terblanche et al., "13C spin-lattice relaxation in natural diamond: Zeeman relaxation in fields of 500 to 5000 G at 300 K due to fixed paramagnetic nitrogen defects," Solid State Nuclear Magnetic Resonance 19: 107-129 (May 2001), 23 pages.
Tetienne et al., "Magnetic-field-dependent photodynamics of single NV defects in diamond: an application to qualitative all-optical magnetic imaging," New Journal of Physics 14(103033): 1-5 (Oct. 2012), 16 pages.
Tetienne, et al. "Spin relaxometry of single nitrogen-vacancy defects in diamond nanocrystals for magnetic noise sensing." Physical Review B 87.23 (Apr. 3, 2013): 235436-1-235436-5.
Tong et al., "A hybrid-system approach for W state and cluster state generation," Optics Communication 310: 166-172, (Jan. 2014; available online Aug. 12, 2013), 7 pages.
Uhlen et al., "New diamond nanofabrication process for hard x-ray zone plates," J. of Vacuum Science & Tech. B 29(6) (06FG03): 1-4 (Nov./Dec. 2011), 4 pages.
U.S. Notice of Allowance dated Apr. 20, 2016, from related U.S. Appl. No. 15/003,718, 9 pages.
U.S. Notice of Allowance dated Aug. 11, 2017 from related U.S. Appl. No. 15/003,558, 5 pages.

(56) References Cited

OTHER PUBLICATIONS

U.S. Notice of Allowance dated Aug. 17, 2016, from related U.S. Appl. No. 15/003,718, 8 pages.
U.S. Notice of Allowance dated Dec. 13, 2016, from related U.S. Appl. No. 14/680,877, 8 pages.
U.S. Notice of Allowance dated Dec. 22, 2016, from related U.S. Appl. No. 14/659,498, 10 pages.
U.S. Notice of Allowance dated Feb. 14, 2017, from related U.S. Appl. No. 15/003,677, 8 pages.
U.S. Notice of Allowance dated Jul. 18, 2017 from related U.S. Appl. No. 15/003,634, 6 pages.
U.S. Notice of Allowance dated Jul. 24, 2017 from related U.S. Appl. No. 15/003,088, 12 pages.
U.S. Notice of Allowance dated Jun. 20, 2017, from related U.S. Appl. No. 15/204,675, 9 pages.
U.S. Notice of Allowance dated Jun. 28, 2017 from related U.S. Appl. No. 15/003,256, 10 pages.
U.S. Notice of Allowance dated Jun. 8, 2017, from related U.S. Appl. No. 15/351,862, 7 pages.
U.S. Notice of Allowance dated Mar. 15, 2017, from related U.S. Appl. No. 15/351,862, 6 pages.
U.S. Notice of Allowance dated Mar. 29, 2016, from related U.S. Appl. No. 15/003,590, 11 pages.
U.S. Notice of Allowance dated May 26, 2017 from related U.S. Appl. No. 15/218,821, 7 pages.
U.S. Notice of Allowance dated Sep. 1, 2017, from related U.S. Appl. No. 14/676,740, 7 pages.
U.S. Notice of Allowance dated Sep. 14, 2017, from related U.S. Appl. No. 15/476,636, 10 pages.
U.S. Notice of Allowance dated Sep. 18, 2017, from related U.S. Appl. No. 15/003,206, 11 pages.
U.S. Notice of Allowance dated Sep. 26, 2017, from related U.S. Appl. No. 15/003,281, 7 pages.
U.S. Notice of Allowance dated Sep. 8, 2016, from related U.S. Appl. No. 15/003,298, 10 pages.
U.S. Office Action dated Apr. 17, 2017, from related U.S. Appl. No. 15/003,558, 12 pages.
U.S. Office Action dated Aug. 15, 2017 from related U.S. Appl. No. 15/003,281, 12 pages.
U.S. Office Action dated Aug. 24, 2016 from related U.S. Appl. No. 14/676,740, 19 pages.
U.S. Office Action dated Feb. 10, 2017, from related U.S. Appl. No. 14/676,740, 20 pages.
U.S. Office Action dated Feb. 10, 2017, from related U.S. Appl. No. 15/003,088, 11 pages.
U.S. Office Action dated Feb. 16, 2017, from related U.S. Appl. No. 15/204,675, 7 pages.
U.S. Office Action dated Jul. 27, 2017 from related U.S. Appl. No. 15/003,577, 15 pages.
U.S. Office Action dated Jul. 29, 2016 from related U.S. Appl. No. 14/680,877, 8 pages.
U.S. Office Action dated Jun. 1, 2017, from related U.S. Appl. No. 15/003,797, 29 pages.
U.S. Office Action dated Jun. 1, 2017, from related U.S. Appl. No. 15/179,957, 29 pages.
U.S. Office Action dated Jun. 12, 2017, from related U.S. Appl. No. 15/003,256, 9 pages.
U.S. Office Action dated Jun. 12, 2017, from related U.S. Appl. No. 15/003,336, 14 pages.
U.S. Office Action dated Jun. 16, 2017, from related U.S. Appl. No. 15/003,678, 15 pages.
U.S. Office Action dated Jun. 2, 2017, from related U.S. Appl. No. 15/476,636, 10 pages.
U.S. Office Action dated Mar. 1, 2017, from related U.S. Appl. No. 15/003,634, 7 pages.
U.S. Office Action dated Mar. 16, 2017, from related U.S. Appl. No. 15/218,821, 7 pages.
U.S. Office Action dated May 13, 2016, from related U.S. Appl. No. 14/676,740, 15 pages.
U.S. Office Action dated May 22, 2017, from related U.S. Appl. No. 15/003,206, 12 pages.
U.S. Office Action dated May 6, 2016, from related U.S. Appl. No. 14/659,498.
U.S. Office Action dated Nov. 2, 2016, from related U.S. Appl. No. 15/003,256, 19 pages.
U.S. Office Action dated Nov. 3, 2016, from related U.S. Appl. No. 15/204,675, 9 pages.
U.S. Office Action dated Oct. 14, 2016 from related U.S. Appl. No. 15/003,677, 13 pages.
U.S. Office Action dated Oct. 19, 2016, from related U.S. Appl. No. 15/218,821, 6 pages.
U.S. Office Action dated Sep. 27, 2017, from related U.S. Appl. No. 15/003,176, 8 pages.
U.S. Office Action dated Sep. 8, 2017, from related U.S. Appl. No. 15/003,292, 8 pages.
Vershovskii & Dmitriev, "Combined excitation of an optically detected magnetic resonance in nitrogen-vacancy centers in diamond for precision measurement of the components of a magnetic field vector," Technical Physics Letters 41(11): 1026-1029 (Nov. 2015), 4 pages.
Vershovskii & Dmitriev, "Micro-scale three-component quantum magnetometer based on nitrogen-vacancy color centers in diamond crystal," Technical Physics Letters 41(4): 393-396 (Apr. 2015), 4 pages.
Wahlstrom et al., "Modeling Magnetic Fields Using Gaussian Processes," 2013 IEEE International Conference on Acoustics, Speech, and Signal Processing, pp. 3522-3526 (May 26-31, 2013), 5 pages.
Wang et al., "Optimizing ultrasensitive single electron magnetometer based on nitrogen-vacancy center in diamond," Chinese Science Bulletin, 58(24): 2920-2923, (Aug. 2013), 4 pages.
Webber et al., "Ab initio thermodynamics calculation of the relative concentration of NV- and NV0 defects in diamond," Physical Review B 85,(014102): 1-7 (Jan. 2012), 7 pages.
Wells, et al. "Assessing graphene nanopores for sequencing DNA." Nano letters 12.8 (Jul. 10, 2012): 4117-4123.
Widmann et al., "Coherent control of single spins in silicon carbide at room temperature," Nature Materials, 14: 164-168 (2015) (available online Dec. 1, 2014), 5 pages.
Wolf et al., "Subpicotesla Diamond Magnetometry," Physical Review X 5(041001): 1-10 (Oct. 2015), 10 pages.
Wolfe et al., "Off-resonant manipulation of spins in diamond via precessing magnetization of a proximal ferromagnet," Physical Review B 89(180406): 1-5 (May 2014), 5 pages.
Wroble, "Performance Analysis of Magnetic Indoor Local Positioning System." Western Michigan University Master's Theses, Paper 609 (Jun. 2015), 42 pages.
Wysocki et al., "Modified Walsh-Hadamard sequences for DS CDMA wireless systems." Int. J. Adaptive Control and Signal Processing 16(8): 589-602 (Oct. 2002; first published online Sep. 23, 2002), 25 pages.
Xue & Liu, "Producing GHZ state of nitrogen-vacancy centers in cavity QED," Journal of Modern Optics 60(6-7), (Mar. 2013), 8 pages.
Yang & Gu, "Novel calibration techniques for high pulsed-magnetic fields using luminescence caused by photo," (with English machine translation), Journal of Huazhong University of Science and Technology, (Jun. 2007), 11 pages.
Yavkin et al., "Defects in Nanodiamonds: Application of High-Frequency cw and Pulse EPR, ODMR," Applied Magnetic Resonance, 45: 1035-1049 (Oct. 2014; published online Sep. 10, 2014), 15 pages.
Yu et al., "Bright fluorescent nanodiamonds: no photobleaching and low cytotoxicity," J. Am. Chem. Soc., 127: 17604-17605 (Nov. 25, 2005), 2 pages.
Zhang et al., "Laser-polarization-dependent and magnetically controlled optical bistability in diamond nitrogen-vacancy centers," Physics Letters A 377: 2621-2627 (Nov. 2013), 7 pages.
Zhang et al., "Laser-polarization-dependent spontaneous emission of the zero phonon line from single nitrogen-vacancy center in diamond," Chinese Physics B 24(3), (Apr. 2014), 13 pages.

(56) References Cited

OTHER PUBLICATIONS

Zhang et al., "Scalable quantum information transfer between nitrogen-vacancy-center ensembles," Annals of Physics, 355: 170-181 (Apr. 2015; available online Feb. 14, 2013), 12 pages.
Zhao et al., "Atomic-scale magnetometry of distant nuclear spin clusters via nitrogen-vacancy spin in diamond," Nature Nanotechnology, 5: 242-246 (Apr. 2011), 5 pages.
U.S. Notice of Allowance dated Oct. 19, 2017, from related U.S. Appl. No. 15/179,957, 5 pages.
U.S. Notice of Allowance dated Oct. 23, 2017, from related U.S. Appl. No. 15/003,797, 6 pages.
U.S. Office Action dated Nov. 24, 2017, from related U.S. Appl. No. 15/003,145, 14 pages.
U.S. Office Action dated Nov. 27, 2017, from related U.S. Appl. No. 15/468,386, 28 pages.
Bui et al., "Noninvasive Fault Monitoring of Electrical Machines by Solving the Steady-State Magnetic Inverse Problem," in IEEE Transactions on Magnetics, vol. 44, No. 6, pp. 1050-1053, Jun. 24, 2008.
Chadebec et al., "Rotor fault detection of electrical machines by low frequency magnetic stray field analysis," 2005 5th IEEE International Symposium on Diagnostics for Electric Machines, Power Electronics and Drives, Vienna, 2005, submitted Mar. 22, 2006, pp. 1-6.
Froidurot et al., "Magnetic discretion of naval propulsion machines," in IEEE Transactions on Magnetics, vol. 38, No. 2, pp. 1185-1188, Mar. 2002.
IEEE Std 802.11 TM-2012 Wireless LAN Medium Access Control (MAC) and Physical Layer (PHY) Specifications, 1 page.
Kwon et al., "Analysis of the far field of permanent-magnet motors and effects of geometric asymmetries and unbalance in magnet design," in IEEE Transactions on Magnetics, vol. 40, No. 2, pp. 435-442, Mar. 2004.
Maertz et al., "Vector magnetic field microscopy using nitrogen vacancy centers in diamond", Applied Physics Letters 96, No. 9, Mar. 1, 2010, pp. 092504-1-092504-3.
U.S. Notice of Allowance dated Feb. 2, 2018, from related U.S. Appl. No. 15/003,292, 8 pages.
U.S. Notice of Allowance dated Feb. 21, 2018, from related U.S. Appl. No. 15/003,176, 9 pages.
U.S. Office Action dated Feb. 1, 2018, from related U.S. Appl. No. 15/003,577, 16 pages.
U.S. Office Action dated Feb. 5, 2018, from related U.S. Appl. No. 15/450,504, 12 pages.
U.S. Office Action dated Jan. 25, 2018, from related U.S. Appl. No. 15/672,953, 28 pages.
U.S. Office Action dated Jan. 26, 2018, from related U.S. Appl. No. 15/003,678, 14 pages.
U.S. Office Action dated Mar. 27, 2018, from related U.S. Appl. No. 15/468,386, 21 pages.
U.S. Office Action dated Mar. 28, 2018, from related U.S. Appl. No. 15/003,177, 12 pages.
U.S. Office Action dated Mar. 5, 2018, from related U.S. Appl. No. 14/866,730, 14 pages.
U.S. Office Action dated Mar. 8, 2018, from related U.S. Appl. No. 15/380,691, 12 pages.
U.S. Office Action dated Mar. 8, 2018, from related U.S. Appl. No. 15/479,256, 30 pages.
Wegerich, "Similarity based modeling of time synchronous averaged vibration signals for machinery health monitoring," 2004 IEEE Aerospace Conference Proceedings (IEEE Cat. No. 04TH8720), 2004, pp. 3654-3662 vol. 6.
Wikipedia, "Continuous phase modulation", downloaded from https://web.archive.org/web/20151017015236/https://en.wikipedia.org/wiki/Continuous_phase_modulation on May 10, 2017, 3 pages.
Wikipedia, "Minimum-shift keying", downloaded from https://web.archive.org/web/20151017175828/https://en.wikipedia.org/wiki/Minimum-shift_keying on May 10, 2017, 2 pages.
European Extended Search Report for Appl. Ser. No. 16743879.5 dated Sep. 11, 2018, 11 pages.
European Extended Search Report for Appl. Ser. No. 16800410.9 dated Oct. 12, 2018, 11 pages.
Niu, "Crack Detection of Power Line Based on Metal Magnetic Memory Non-destructive", TELKOMNIKA Indonesian Journal of Electrical Engineering, vol. 12, No. 11, Nov. 1, 2014, pp. 7764-7771.
U.S. Final Office Action for U.S. Appl. No. 15/380,691 dated Sep. 21, 2018, 12 pages.
U.S. Final Office Action for U.S. Appl. No. 15/479,256 dated Sep. 10, 2018, 20 pages.
U.S. Non-Final Office Action for U.S. Appl. No. 15/443,422 dated Oct. 2, 2018, 16 pages.
U.S. Non-Final Office Action for U.S. Appl. No. 15/446,373 dated Oct. 1, 2018, 13 pages.
U.S. Non-Final Office Action for U.S. Appl. No. 15/454,162 dated Sep. 10, 2018, 13 pages.
U.S. Non-Final Office Action for U.S. Appl. No. 15/468,282 dated Oct. 10, 2018, 12 pages.
U.S. Non-Final Office Action for U.S. Appl. No. 15/372,201 dated Oct. 15, 2018, 12 pages.
U.S. Non-Final Office Action for U.S. Appl. No. 15/468,274 dated Oct. 26, 2018, 11 pages.
U.S. Notice of Allowance for U.S. Appl. No. 14/866,730 dated Aug. 15, 2018, 9 pages.
U.S. Notice of Allowance for U.S. Appl. No. 15/468,289 dated Oct. 17, 2018, 12 pages.
U.S. Notice of Allowance for U.S. Appl. No. 15/003,704 dated Nov. 2, 2018, 19 pages.
U.S. Appl. No. 14/659,498, filed Mar. 16, 2015, U.S. Pat. No. 9,638,821.
PCT/US2015/021093, Mar. 17, 2015, WO2015142945.
U.S. Appl. No. 14/676,740, filed Apr. 1, 2015, 20150326410.
PCT/US2015/024265, Apr. 3. 2015, WO2015157110.
PCT/US2015/024723, Apr. 7, 2015, WO2015157290.
U.S. Appl. No. 14/680,877, filed Apr. 7, 2015, U.S. Pat. No. 9,590,601.
U.S. Appl. No. 14/866,730, filed Sep. 25, 2015, 20160146904.
U.S. Appl. No. 15/003,678, filed Jan. 21, 2016, 20170212183.
U.S. Appl. No. 15/003,281, filed Jan. 21. 2016, 20170212178.
U.S. Appl. No. 15/003,292, filed Jan. 21, 2016, 20170212179.
U.S. Appl. No. 15/003,298, filed Jan. 21, 2016, U.S. Pat. No. 9,551,763.
U.S. Appl. No. 15/003,309, filed Jan. 21, 2016, 20170212180.
U.S. Appl. No. 15/003,176, filed Jan. 21, 2016, 20170123015.
U.S. Appl. No. 15/003,145, filed Jan. 21, 2016, 201701990156.
U.S. Appl. No. 15/003,336, filed Jan. 21, 2016, 20170212181.
U.S. Appl. No. 15/003,558, filed Jan. 21, 2016, 20170146617.
U.S. Appl. No. 15/003,519, filed Jan. 21, 2016, 20170146616.
U.S. Appl. No. 15/003,677, filed Jan. 21, 2016, U.S. Pat. No. 9,614,589.
U.S. Appl. No. 15/003,256, filed Jan. 21, 2016, 20170212177.
U.S. Appl. No. 15/003,577, filed Jan. 21, 2016, 20170212046.
U.S. Appl. No. 15/003,704, filed Jan. 21, 2016, 20160231394.
U.S. Appl. No. 15/003,718, filed Jan. 21, 2016, U.S. Pat. No. 9,541,610.
U.S. Appl. No. 15/003,062, filed Jan. 21, 2016, 20170023487.
U.S. Appl. No. 15/003,652, filed Jan. 21, 2016, 20170010594.
U.S. Appl. No. 15/003,634, filed Jan. 21, 2016, 20170212182.
U.S. Appl. No. 15/003,670, filed Jan. 21, 2016, 20170212190.
U.S. Appl. No. 15/003,088, filed Jan. 21, 2016, 20160214714.
U.S. Appl. No. 15/003,797, filed Jan. 21, 2016, 20160216341.
U.S. Appl. No. 15/003,590, filed Jan. 21, 2016, U.S. Pat. No. 9,557,391.
U.S. Appl. No. 15/003,206, filed Jan. 21, 2016, 20170110015.
U.S. Appl. No. 15/003,193, filed Jan. 21, 2016, 20160216304.
U.S. Appl. No. 15/003,617, filed Jan. 21, 2016, 20170020334.
U.S. Appl. No. 15/003,396, filed Jan. 21, 2016, 20170068012.
U.S. Appl. No. 15/003,177, filed Jan. 21, 2016, 20170212258.
U.S. Appl. No. 15/003,209, filed Jan. 21, 2016, 20170211947.
PCT/US2016/014389, Jan. 21, 2016, WO2017078766.
PCT/US2016/014336, Jan. 21, 2016, WO2016118756.
PCT/US2016/014403, Jan. 21, 2016, WO2016118791.
PCT/US2016/014331, Jan. 21, 2016, WO2016126435.

(56) References Cited

OTHER PUBLICATIONS

PCT/US2016/014387, Jan. 21, 2016, WO2017014807.
PCT/US2016/014390, Jan. 21, 2016, WO2016190909.
PCT/US2016/014385, Jan. 21, 2016, WO2016122966.
PCT/US2016/014375, Jan. 21, 2016, WO2016122965.
PCT/US2016/014298, Jan. 21, 2016, WO2017007514.
PCT/US2016/014297, Jan. 21, 2016, WO2017007513.
PCT/US2016/014377, Jan. 21, 2016, WO2017039747.
PCT/US2016/014392, Jan. 21, 2016, WO2017127095.
PCT/US2016/014395, Jan. 21, 2016, WO2017127097.
PCT/US2016/014394, Jan. 21, 2016, WO2017127096.
PCT/US2016/014386, Jan. 21, 2016, WO2017127094.
PCT/US2016/014333, Jan. 21, 2016, WO2016126436.
PCT/US2016/014328, Jan. 21, 2016, WO2017087014.
PCT/US2016/014325, Jan. 21, 2016, WO2017087013.
PCT/US2016/014330, Jan. 21, 2016, WO2017127085.
PCT/US2016/014388, Jan. 21, 2016, WO2017095454.
PCT/US2016/014380, Jan. 21, 2016, WO2017123261.
PCT/US2016/014290, Jan. 21, 2016, WO2017127080.
PCT/US2016/014363, Jan. 21, 2016, WO2017127090.
PCT/US2016/014287, Jan. 21, 2016, WO2017127079.
PCT/US2016/014291, Jan. 21, 2016, WO2017127081.
PCT/US2016/014396, Jan. 21, 2016, WO2017127098.
PCT/US2016/014384, Jan. 21, 2016, WO2017127093.
PCT/US2016/014376, Jan. 21, 2016, WO2017127091.
U.S. Appl. No. 15/179,957, filed Jun. 10, 2016, 20160356863.
U.S. Appl. No. 15/207,457, filed Jul. 11, 2016.
U.S. Appl. No. 15/218,821, filed Jul. 25, 2016, 20170212185.
U.S. Appl. No. 15/204,675, filed Jul. 7, 2016, 20170212184.
U.S. Appl. No. 15/350,303, filed Nov. 14, 2016.
U.S. Appl. No. 15/351,862, filed Nov. 15, 2016, U.S. Pat. No. 9,720,055.
U.S. Appl. No. 15/372,201, filed Dec. 7, 2016, 20170212187.
U.S. Appl. No. 15/376,244, filed Dec. 12, 2016.
PCT/US2016/066566, Dec. 14, 2016.
U.S. Appl. No. 15/380,691, filed Dec. 15, 2016.
U.S. Appl. No. 15/382,045, filed Dec. 16, 2016.
U.S. Appl. No. 15/380,419, filed Dec. 15, 2016.
PCT/US2016/068320, Dec. 22, 2016.
PCT/US2016/068344, Dec. 22, 2016.
PCT/US2016/068366, Dec. 22, 2016.
U.S. Appl. No. 15/419,832, filed Jan. 30, 2017, 20170139017.
U.S. Appl. No. 15/400,794, filed Jan. 6, 2017, 20170115361.
U.S. Appl. No. 15/443,422, filed Feb. 27, 2017.
PCT/US2017/017321, Feb. 10, 2017.
PCT/US2017/018099, Feb. 16, 2017.
U.S. Appl. No. 15/437,222, filed Feb. 20, 2017, 20170120293.
U.S. Appl. No. 15/437,038, filed Feb. 20, 2017.
PCT/US2017/018709, Feb. 21, 2017.
PCT/US2017/018701, Feb. 21, 2017.
U.S. Appl. No. 15/440,194, filed Feb. 23, 2017.
PCT/US2017/019411, Feb. 24, 2017.
U.S. Appl. No. 15/446,373, filed Mar. 1, 2017.
U.S. Appl. No. 15/450,504, filed Mar. 6, 2017.
U.S. Appl. No. 15/454,162, filed Mar. 9, 2017.
PCT/US2017/021593, Mar. 9, 2017.
PCT/US2017/021811, Mar. 10, 2017.
U.S. Appl. No. 15/456,913, filed Mar. 13, 2017.
PCT/US2017/022118, Mar. 13, 2017.
PCT/US2017/022279, Mar. 14, 2017.
U.S. Appl. No. 15/468,356, filed Mar. 24, 2017.
U.S. Appl. No. 15/468,397, filed Mar. 24, 2017.
U.S. Appl. No. 15/468,386, filed Mar. 24, 2017.
U.S. Appl. No. 15/468,289, filed Mar. 24, 2017.
U.S. Appl. No. 15/468,641, filed Mar. 24, 2017.
U.S. Appl. No. 15/468,582, filed Mar. 24, 2017.
U.S. Appl. No. 15/468,410, filed Mar. 24, 2017.
U.S. Appl. No. 15/468,951, filed Mar. 24, 2017.
U.S. Appl. No. 15/468,559, filed Mar. 24, 2017.
U.S. Appl. No. 15/468,282, filed Mar. 24, 2017.
U.S. Appl. No. 15/468,314, filed Mar. 24, 2017.
U.S. Appl. No. 15/468,274, filed Mar. 24, 2017.
U.S. Appl. No. 15/468,303, filed Mar. 24, 2017.
U.S. Appl. No. 15/469,374, filed Mar. 24, 2017.
PCT/US2017/024165, Mar. 24, 2017.
PCT/US2017/024167, Mar. 24, 2017.
PCT/US2017/024168, Mar. 24, 2017.
PCT/US2017/024169, Mar. 24, 2017.
PCT/US2017/024171, Mar. 24, 2017.
PCT/US2017/024172, Mar. 24, 2017.
PCT/US2017/024173, Mar. 24, 2017.
PCT/US2017/024174, Mar. 24, 2017.
PCT/US2017/024175, Mar. 24, 2017.
PCT/US2017/024177, Mar. 24, 2017.
PCT/US2017/024179, Mar. 24, 2017.
PCT/US2017/024180, Mar. 24, 2017.
PCT/US2017/024181, Mar. 24, 2017.
PCT/US2017/024182, Mar. 24, 2017.
U.S. Appl. No. 15/476,636, filed Mar. 31, 2017, 20170205526.
U.S. Appl. No. 15/479,256, filed Apr. 4, 2017, 20170207823.
U.S. Appl. No. 15/610,526, filed May 31, 2017.
PCT/US2017/035315, May 31, 2017.
U.S. Appl. No. 15/672,953, filed Aug. 9, 2017.
European Extended Search Report for Appl. Ser. No. 16740794.9 dated Nov. 12, 2018, 12 pages.
Halbach et al., "Design of Permanent Multipole Magnets with Oriented Rare Earth Cobalt Material", Nuclear Instruments and Methods, North Holland Publishing Co., Amsterdam, NL., vol. 169, Jan. 1, 1980, pp. 1-5, XP001032085, DOI: 10.1016/0029-554X(80)90094-4.
International Search Report and Written Opinion for PCT Appl. Appl. Ser. No. PCT/US2018/041527 dated Feb. 4, 2019, 22 pages.
U.S. Ex Parte Quayle Action for U.S. Appl. No. 15/468,641 dated Nov. 28, 2018, 11 pages.
U.S. Non-Final Office Action for U.S. Appl. No. 15/003,177 dated Jan. 14, 2019, 15 pages.
U.S. Non-Final Office Action for U.S. Appl. No. 15/003,670 dated Nov. 27, 2018, 14 pages.
U.S. Non-Final Office Action for U.S. Appl. No. 15/382,045 dated Dec. 31, 2018, 16 pages.
U.S. Non-Final Office Action for U.S. Appl. No. 15/400,794 dated Jan. 10, 2019, 6 pages.
U.S. Non-Final Office Action for U.S. Appl. No. 15/468,356 dated Jan. 2, 2019, 10 pages.
U.S. Non-Final Office Action for U.S. Appl. No. 15/468,951 dated Dec. 13, 2018, 9 pages.
U.S. Notice of Allowance for U.S. Appl. No. 15/003,670 dated Feb. 1, 2019, 7 pages.
U.S. Notice of Allowance for U.S. Appl. No. 15/350,303 dated Dec. 26, 2018, 10 pages.
U.S. Notice of Allowance for U.S. Appl. No. 15/450,504 dated Dec. 13, 2018, 7 pages.
U.S. Notice of Allowance for U.S. Appl. No. 15/454,162 dated Jan. 17, 2019, 8 pages.
U.S. Notice of Allowance for U.S. Appl. No. 15/468,641 dated Feb. 7, 2019, 10 pages.
U.S. Notice of Allowance for U.S. Appl. No. 15/479,256 dated Feb. 4, 2019, 7 pages.
Rosskopf, T., "Advanced quantum sensing using nitrogen vacancy centers in diamond", Dissertation, Jul. 5, 2017, p. 91 (12 pages), <https://epo.summon.serialssolutions.com/2.0.0/link/0/elvHCXMw Y2BQsUxJMUs0MJTWNQWwlomgZYWuolJ5qa6qaagq5BSjEzM LUG7kSOdTULczYPcTXwQHUXQgkrUWXXQ a21WpJRpZukC 26gWBhZmjEzsAjbAuaWkH1HrEqAZSlojWVyZkkqUoXhJsjA44 100S3EwJSaJ8lg5AidcFcoLAV6qDRXoRiOfDwvXaEUTAJzV1E-MElVyllKTQYWeAmJlJLB5ppCZpwCMRmCCSRFlMHVzDXH201X>.
Schonfeld, R.S., "Optical readout of single spins for quantum computing and magnetic sensing", Dissertation, Fachbereich Physlk der Freien Universitat Berlin, May 1, 2011, 21 Pages (relevant pages only), <http://www.diss.fu-berlin.de/diss/serviets/ MCRFileNodeServiceUFU DISS derivate 000000012199/ Dissertation Simon-choenfela PublicVersion-2.pdfJsessionid-89A943688E59>.

(56) References Cited

OTHER PUBLICATIONS

International Search Report and Written Opinion for PCT Appl. U.S. Ser. No. PCT/US2018/041411 dated Feb. 8, 2019, 13 pages.
U.S. Non-Final Office Action for U.S. Appl. No. 15/419,832 dated Feb. 8, 2019, 12 pages.
U.S. Non-Final Office Action for U.S. Appl. No. 15/003,309 dated Feb. 13, 2019, 16 pages.
U.S. Non-Final Office Action for U.S. Appl. No. 15/440,194 dated Feb. 15, 2019, 21 pages.
U.S. Notice of Allowance for U.S. Appl. No. 15/468,282 dated Feb. 19, 2019, 8 pages.
U.S. Notice of Allowance for U.S. Appl. No. 15/376,244 dated Feb. 21, 2019, 7 pages.
U.S. Non-Final Office Action for U.S. Appl. No. 15/003,617 dated Feb. 26, 2019 (10 pp.).
U.S. Notice of Allowance for U.S. Appl. No. 15/380,419 dated Feb. 26, 2019, 5 pages.
U.S. Non-Final Office Action for U.S. Appl. No. 15/469,374 dated Feb. 28, 2019, 14 pages.
U.S. Notice of Allowance for U.S. Appl. No. 15/207,457 dated Mar. 6, 2019, 16 pages.
U.S. Final Office Action for U.S. Appl. No. 15/443,422 dated Mar. 7, 2019, 17 pages.

\* cited by examiner

HIGH SPEED SEQUENTIAL CANCELLATION FOR PULSED MODE

FIELD

The subject technology generally relates without limitation to magnetometers, and for example, to a high speed sequential cancellation for pulsed mode.

BACKGROUND

A number of industrial applications, as well as scientific areas such as physics and chemistry can benefit from magnetic detection and imaging with a device that has extraordinary sensitivity, ability to capture signals that fluctuate very rapidly (bandwidth) all with a substantive package that is extraordinarily small in size and efficient in power. Many advanced magnetic imaging systems can operate in restricted conditions, for example, high vacuum and/or cryogenic temperatures, which can make them inapplicable for imaging applications that require ambient or other conditions. Furthermore, small size, weight and power (SWAP) magnetic sensors of moderate sensitivity, vector accuracy, and bandwidth are valuable in many applications.

SUMMARY

Some embodiments provide methods and systems for high bandwidth acquisition of magnetometer data with increased sensitivity. In some implementations, a reference signal may be utilized prior to acquisition of a measured signal for a magnetometer. This reference signal may provide a full repolarization of a magneto-optical defect center material prior to acquiring the reference signal. The reference signal may then be used to adjust the measured signal to correct for potential fluctuations in optical excitation power levels, which can cause a proportional fluctuation in the measured signal. However, such a full repolarization and added reference signal before each measured signal may reduce the bandwidth of the magnetometer and may also increase measurement noise, and therefore decrease sensitivity, by including noise from the reference signal when calculating the resulting processed signal. To increase bandwidth and sensitivity, the reference signal may be omitted such that only a radiofrequency (RF) pulse excitation sequence is included between measurements. In some implementations, a fixed "system rail" photo measurement may be obtained initially and used as a fixed reference signal for subsequent measured signals. The fixed, nominal reference signal can substantially compensate for intensity shifts for the magnetometer without decreasing bandwidth or sensitivity. In other implementations, additional signal processing may be utilized to adjust for drift, jitter, or other variations in intensity levels.

Some embodiments may include a magnetometer and a controller. The magnetometer may include a magneto-optical defect center material, an optical excitation source, a radiofrequency (RF) excitation source, and an optical sensor. The controller may be configured to activate a radiofrequency (RF) pulse sequence for the RF excitation source to apply a RF field to the magneto-optical defect center material, acquire a nominal ground reference signal for the magneto-optical defect center material, and acquire a magnetic field measurement from the magneto-optical defect center material using the optical sensor. The magnetic field measurement may be acquired independent of a reference magnetic field measurement.

In some implementations, acquiring the repetitive magnetic field measurement can include a polarization pulse length. In some implementations, the controller may processes the repetitive magnetic field measurement directly to obtain magnetometry measurements. In some implementations, the controller may further be configured to determine a vector of the repetitive magnetic field measurement. In some implementations, the controller may use a fixed system rail photo measurement as a nominal reference value. The magneto-optical defect center material may be a diamond having nitrogen vacancies. The controller may be further configured to process the magnetic field measurement.

Other implementations may relate to a method for operating a magnetometer having a magneto-optical defect center material. The method may include activating a radiofrequency (RF) pulse sequence to apply an RF field to the magneto-optical defect center material, acquiring a nominal ground reference signal for the magneto-optical defect center material, and acquiring a magnetic field measurement using the magneto-optical defect center material. The magnetic field measurement may be acquired independent of a reference magnetic field measurement.

In some implementations, acquiring the magnetic field measurement can include a polarization pulse length. In some implementations, acquiring a magnetic field measurement may include processing the magnetic field measurement directly to obtain magnetometry measurements. In some implementations, the method may further include determining a vector of the repetitive magnetic field measurement. In some implementations, acquiring a magnetic field measurement may include using a fixed system rail photo measurement as a nominal reference value. The magneto-optical defect center material may be a diamond having nitrogen vacancies. The method can further include processing the magnetic field measurement using a controller.

Yet other implementations relate to a sensor that may include a magneto-optical defect center material, a radiofrequency (RF) excitation source, and a controller. The controller may be configured to activate a radiofrequency (RF) pulse sequence for the RF excitation source to apply a RF field to the magneto-optical defect center material, acquire a nominal ground reference signal for the magneto-optical defect center material, and acquire a magnetic field measurement from the magneto-optical defect center material. The magnetic field measurement may be acquired independent of a reference magnetic field measurement.

In some implementations, acquiring the magnetic field measurement can include a polarization pulse length. In some implementations, the controller may processes the magnetic field measurement directly to obtain magnetometry measurements. In some implementations, the controller may further be configured to determine a vector of the magnetic field measurement. In some implementations, the controller may use a fixed system rail photo measurement as a nominal reference value. The magneto-optical defect center material may be a diamond having nitrogen vacancies. The controller may be further configured to process the magnetic field measurement.

BRIEF DESCRIPTION OF THE DRAWINGS

The details of one or more implementations are set forth in the accompanying drawings and the description below.

Other features, aspects, and advantages of the disclosure will become apparent from the description, the drawings, and the claims, in which:

It will be recognized that some or all of the figures are schematic representations for purposes of illustration. The figures are provided for the purpose of illustrating one or more embodiments with the explicit understanding that they will not be used to limit the scope or the meaning of the claims.

DETAILED DESCRIPTION

Following below are more detailed descriptions of various concepts related to, and implementations of, methods, apparatuses, and systems for high bandwidth acquisition of magnetometer data with increased sensitivity. Some embodiments increase bandwidth and sensitivity of the magnetometer by eliminating the need for a reference signal that requires full repolarization of the magneto-optical defect center material prior to acquisition. Eliminating the reference signal eliminates the time needed to repolarize the magneto-optical defect center material and the acquisition time for the reference signal. An optional ground reference, a fixed "system rail" photo measurement, and/or additional signal processing may be utilized to adjust for variations in intensity levels.

Atomic-sized magneto-optical defect centers, such as nitrogen-vacancy (NV) centers in diamond lattices, have excellent sensitivity for magnetic field measurement and enable fabrication of small magnetic sensors. Magneto-optical defect center materials include but are not limited to diamonds, Silicon Carbide (SiC), Phosphorous, and other materials with nitrogen, boron, carbon, silicon, or other defect centers. The diamond nitrogen vacancy (DNV) sensors are maintained in room temperature and atmospheric pressure and can be even used in liquid environments. A green optical source (e.g., a micro-LED) can optically excite NV centers of the DNV sensor and cause emission of fluorescence radiation (e.g., red light) under off-resonant optical excitation. A magnetic field generated, for example, by a microwave coil can probe triplet spin states (e.g., with ms=−1, 0, +1) of the NV centers to split in relation to an external magnetic field projected along the NV axis, resulting in two spin resonance frequencies. The difference between the two spin resonance frequencies can correlate to a measure of the strength of the external magnetic field. A photo detector can measure the fluorescence (red light) emitted by the optically excited NV centers.

Figure 1:
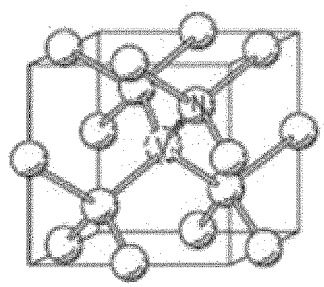
FIG. 1 illustrates an orientation of an NV center in a diamond lattice.

Nitrogen-vacancy centers (NV centers) are defects in a diamond's crystal structure, which can purposefully be manufactured in synthetic diamonds as shown in FIG. 1. In general, when excited by green light and microwave radiation, the NV centers cause the diamond to generate red light. When excited with green light, the NV defect centers generate red light fluorescence. After sufficient time (on order of nanoseconds to microseconds) the fluorescence counts stabilize. When microwave radiation is added, the NV electron spin states are changed, and this results in a change in intensity of the red fluorescence. The changes in fluorescence may be recorded as a measure of electron spin resonance. By measuring the changes, the NV centers may be used to accurately detect the magnetic field strength.

The NV center may exist in a neutral charge state or a negative charge state. Conventionally, the neutral charge state uses the nomenclature $NV^0$, while the negative charge state uses the nomenclature NV, which is adopted in this description.

The NV center may have a number of electrons, including three unpaired electrons, each one from the vacancy to a respective of the three carbon atoms adjacent to the vacancy, and a pair of electrons between the nitrogen and the vacancy. The NV center, which is in the negatively charged state, also includes an extra electron.

Figure 2:
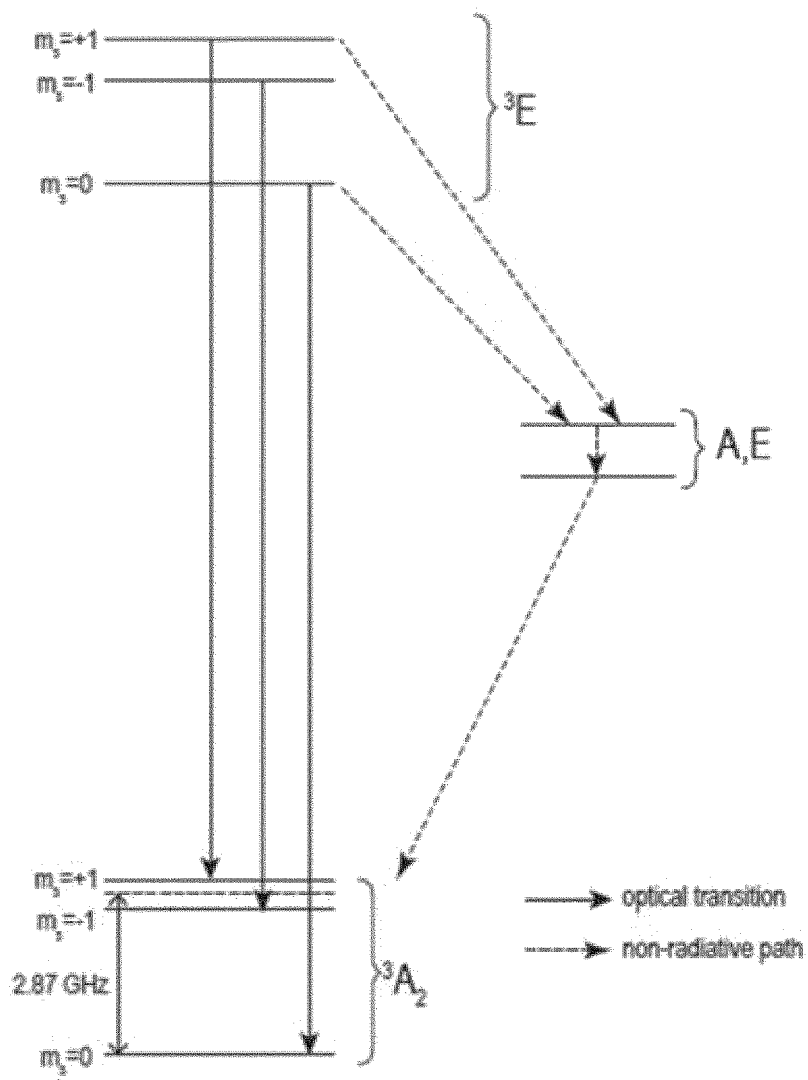
FIG. 2 illustrates an energy level diagram showing energy levels of spin states for the NV center.

The NV center has rotational symmetry and, as shown in FIG. 2, has a ground state, which is a spin triplet with $^3A_2$ symmetry with one spin state $m_s=0$, and two further spin states $m_s=+1$, and $m_s=-1$. In the absence of an external magnetic field, the $m_s=\pm 1$ energy levels are offset from the $m_s=0$ due to spin-spin interactions, and the $m_s=\pm 1$ energy levels are degenerate, i.e., they have the same energy. The $m_s=0$ spin state energy level is split from the $m_s=\pm 1$ energy levels by an energy of approximately 2.87 GHz for a zero external magnetic field.

Introducing an external magnetic field with a component along the NV axis lifts the degeneracy of the $m_s=\pm 1$ energy levels, splitting the energy levels $m_s=\pm 1$ by an amount $2g\mu_B B_z$, where g is the Lande g-factor, $\mu_B$ is the Bohr magneton, and $B_z$ is the component of the external magnetic field along the NV axis. This relationship is correct to a first order and inclusion of higher order corrections is a straightforward matter.

The NV center electronic structure further includes an excited triplet state $^3E$ with corresponding $m_s=0$ and $m_s=\pm 1$ spin states. The optical transitions between the ground state $^3A_2$ and the excited triplet $^3E$ are predominantly spin conserving, meaning that the optical transitions are between initial and final states that have the same spin. For a direct transition between the excited triplet $^3E$ and the ground state $^3A_2$, a photon of red light is emitted with a photon energy corresponding to the energy difference between the energy levels of the transitions.

There is, however, an alternative non-radiative decay route from the triplet $^3E$ to the ground state $^3A_2$ via intermediate electron states, which are thought to be intermediate singlet states A, E with intermediate energy levels. Significantly, the transition rate from the $m_s=\pm1$ spin states of the excited triplet $^3E$ to the intermediate energy levels is significantly greater than the transition rate from the $m_s=0$ spin state of the excited triplet $^3E$ to the intermediate energy levels. The transition from the singlet states A, E to the ground state triplet $^3A_2$ predominantly decays to the $m_s=0$ spin state over the $m_s=\pm1$ spins states. These features of the decay from the excited triplet $^3E$ state via the intermediate singlet states A, E to the ground state triplet $^3A_2$ allows that if optical excitation is provided to the system, the optical excitation will eventually pump the NV center into the $m_s=0$ spin state of the ground state $^3A_2$. In this way, the population of the $m_s=0$ spin state of the ground state $^3A_2$ may be "reset" to a maximum polarization determined by the decay rates from the triplet $^3E$ to the intermediate singlet states.

Another feature of the decay is that the fluorescence intensity due to optically stimulating the excited triplet $^3E$ state is less for the $m_s=\pm1$ states than for the $m_s=0$ spin state. This is so because the decay via the intermediate states does not result in a photon emitted in the fluorescence band, and because of the greater probability that the $m_s=\pm1$ states of the excited triplet $^3E$ state will decay via the non-radiative decay path. The lower fluorescence intensity for the $m_s=\pm1$ states than for the $m_s=0$ spin state allows the fluorescence intensity to be used to determine the spin state. As the population of the $m_s=\pm1$ states increases relative to the $m_s=0$ spin, the overall fluorescence intensity will be reduced.

Figure 3:
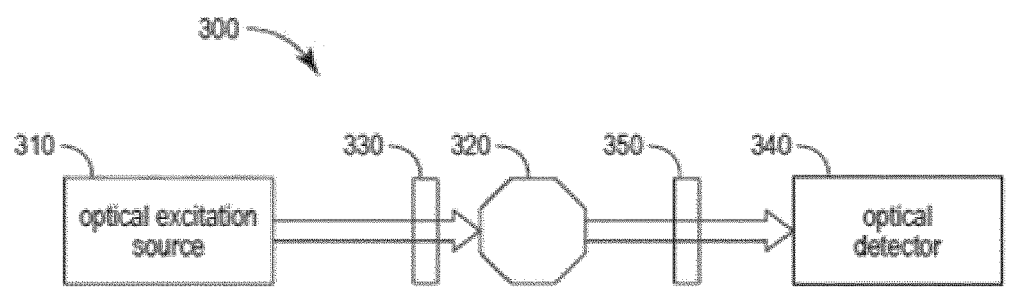
FIG. 3 illustrates a schematic diagram of a NV center magnetic sensor system.

FIG. 3 is a schematic diagram illustrating a NV center magnetic sensor system 300 that uses fluorescence intensity to distinguish the $m_s=\pm1$ states, and to measure the magnetic field based on the energy difference between the $m_s=+1$ state and the $m_s=-1$ state, as manifested by the RF frequencies corresponding to each state. The system 300 includes an optical excitation source 310, which directs optical excitation to an NV diamond material 320 with NV centers. The system further includes an RF excitation source 330, which provides RF radiation to the NV diamond material 320. Light from the NV diamond may be directed through an optical filter 350 to an optical detector 340.

The RF excitation source 330 may be a microwave coil, for example. The RF excitation source 330, when emitting RF radiation with a photon energy resonant with the transition energy between ground $m_s=0$ spin state and the $m_s=+1$ spin state, excites a transition between those spin states. For such a resonance, the spin state cycles between ground $m_s=0$ spin state and the $m_s=+1$ spin state, reducing the population in the $m_s=0$ spin state and reducing the overall fluorescence at resonances. Similarly, resonance and a subsequent decrease in fluorescence intensity occurs between the $m_s=0$ spin state and the $m_s=-1$ spin state of the ground state when the photon energy of the RF radiation emitted by the RF excitation source is the difference in energies of the $m_s=0$ spin state and the $m_s=-1$ spin state.

The optical excitation source 310 may be a laser or a light emitting diode, for example, which emits light in the green (light having a wavelength such that the color is green), for example. The optical excitation source 310 induces fluorescence in the red, which corresponds to an electronic transition from the excited state to the ground state. Light from the NV diamond material 320 is directed through the optical filter 350 to filter out light in the excitation band (in the green, for example), and to pass light in the red fluorescence band, which in turn is detected by the detector 340. The optical excitation light source 310, in addition to exciting fluorescence in the diamond material 320, also serves to reset the population of the $m_s=0$ spin state of the ground state $^3A_2$ to a maximum polarization, or other desired polarization.

Figure 4:
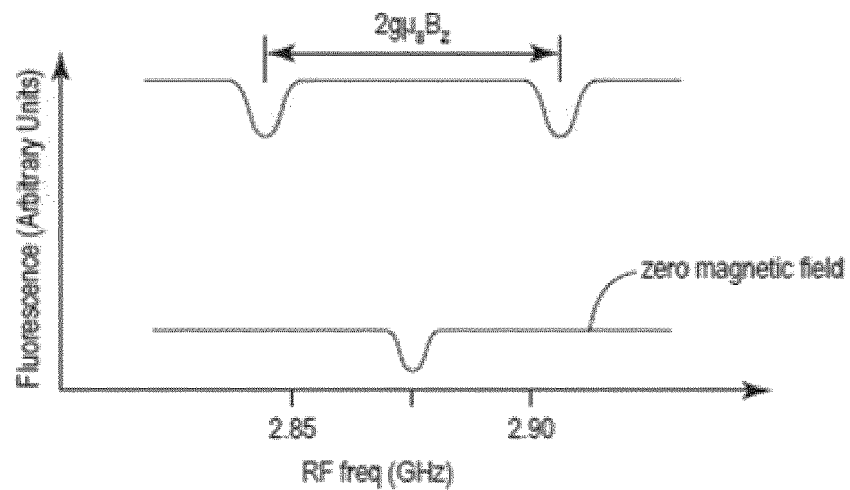
FIG. 4 is a graph illustrating the fluorescence as a function of an applied RF frequency of an NV center along a given direction for a zero magnetic field, and also for a non-zero magnetic field having a component along the NV axis.

For continuous wave excitation, the optical excitation source 310 continuously pumps the NV centers, and the RF excitation source 330 sweeps across a frequency range that includes the zero splitting (when the $m_s=\pm1$ spin states have the same energy) photon energy of approximately 2.87 GHz. The fluorescence for an RF sweep corresponding to a diamond material 320 with NV centers aligned along a single direction is shown in FIG. 4 for different magnetic field components $B_z$ along the NV axis, where the energy splitting between the $m_s=-1$ spin state and the $m_s=+1$ spin state increases with $B_z$. Thus, the component $B_z$ may be determined. Optical excitation schemes other than continuous wave excitation are contemplated, such as excitation schemes involving pulsed optical excitation, and pulsed RF excitation. Examples of pulsed excitation schemes include Ramsey pulse sequence (described in more detail below), spin echo pulse sequence, etc.

Figure 5:
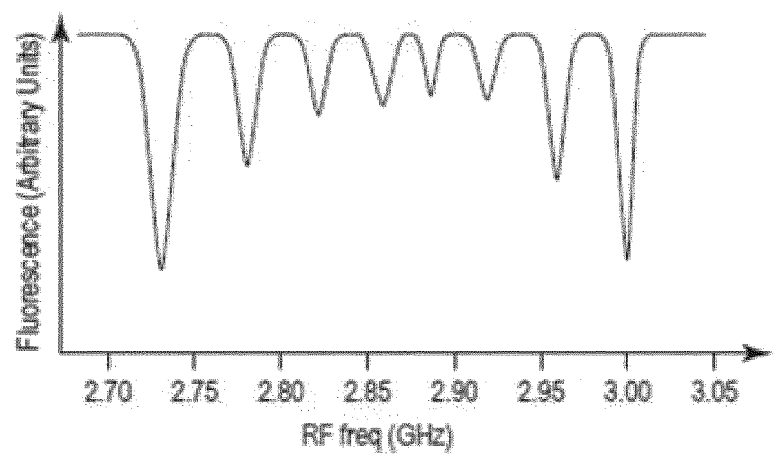
FIG. 5 is a graph illustrating the fluorescence as a function of an applied RF frequency for four different NV center orientations for a non-zero magnetic field.

In general, the diamond material 320 will have NV centers aligned along directions of four different orientation classes. FIG. 5 illustrates fluorescence as a function of RF frequency for the case where the diamond material 320 has NV centers aligned along directions of four different orientation classes. In this case, the component $B_z$ along each of the different orientations may be determined. These results, along with the known orientation of crystallographic planes of a diamond lattice, allow not only the magnitude of the external magnetic field to be determined, but also the direction of the magnetic field.

While FIG. 3 illustrates an NV center magnetic sensor system 300 with NV diamond material 320 with a plurality of NV centers, in general, the magnetic sensor system may instead employ a different magneto-optical defect center material, with a plurality of magneto-optical defect centers. Magneto-optical defect center materials include but are not be limited to diamonds, Silicon Carbide (SiC), Phosphorous, and other materials with nitrogen, boron, carbon, silicon, or other defect centers. The electronic spin state energies of the magneto-optical defect centers shift with magnetic field, and the optical response, such as fluorescence, for the different spin states is not the same for all of the different spin states. In this way, the magnetic field may be determined based on optical excitation, and possibly RF excitation, in a corresponding way to that described above with NV diamond material.

Figure 6:
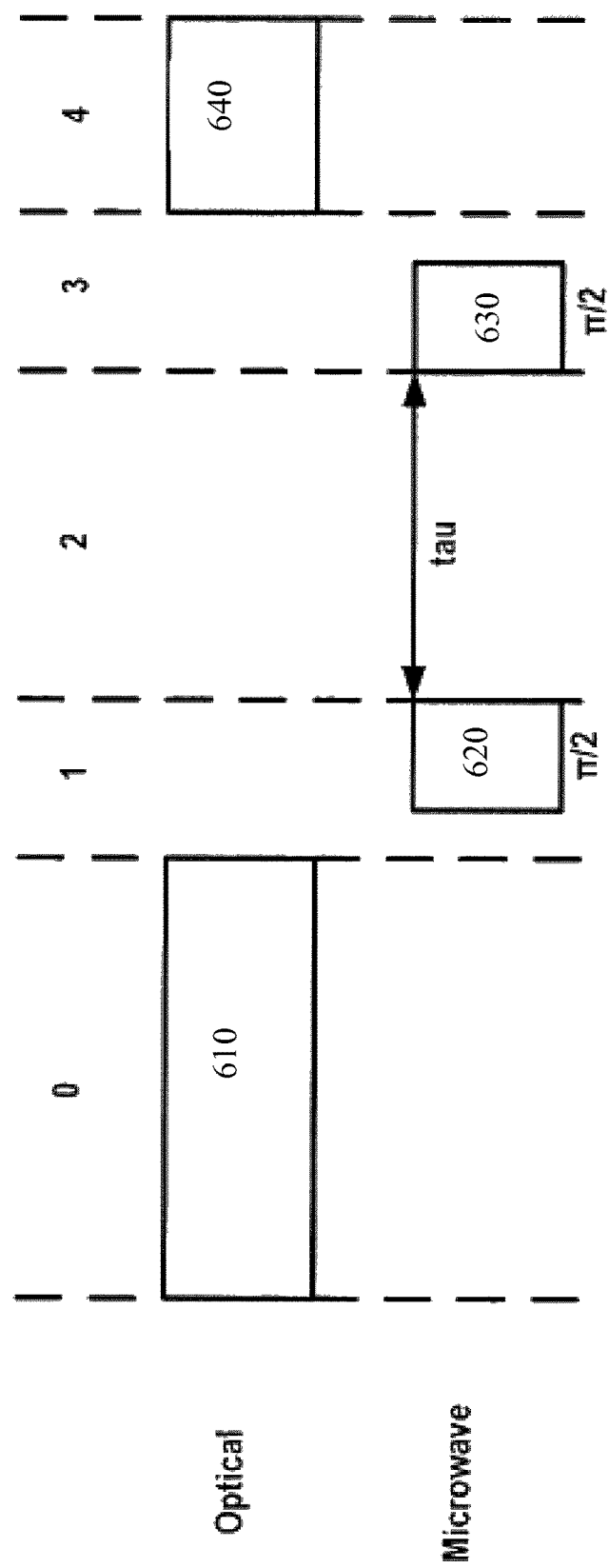
FIG. 6 is a graphical diagram depicting a Ramsey pulse sequence.

A Ramsey pulse sequence is a pulsed RF laser scheme that is believed to measure the free precession of the magnetic moment in the diamond material 320 with NV centers, and is a technique that quantum mechanically prepares and samples the electron spin state. FIG. 6 is an example of a schematic diagram illustrating the Ramsey pulse sequence. As shown in FIG. 6, a Ramsey pulse sequence includes optical excitation pulses and RF excitation pulses over a five-step period. In a first step, during a period 0, a first optical excitation pulse 610 is applied to the system to optically pump electrons into the ground state (i.e., $m_s=0$ spin state). This is followed by a first RF excitation pulse 620 (in the form of, for example, a microwave (MW) $\pi/2$ pulse) during a period 1. The first RF excitation pulse 620 sets the system into superposition of the $m_s=0$ and $m_s=+1$ spin states (or, alternatively, the $m_s=0$ and $m_s=-1$ spin states, depending on the choice of resonance location). During a period 2, the system is allowed to freely precess (and dephase) over a time period referred to as tau ($\tau$). During this free precession time period, the system measures the local magnetic field and serves as a coherent integration. Next, a second RF excitation pulse 630 (in the form of, for example, a MW $\pi/2$ pulse) is applied during a period 3 to project the system back to the $m_s=0$ and $m_s=+1$ basis. Finally, during a period 4, a second optical pulse 640 is applied to optically sample the system and a measurement basis is obtained by detecting the fluorescence intensity of the system. The RF excitation pulses applied are provided at a given RF frequency in relation to the Lorentzians such as referenced in connection with FIG. 5.

Figure 7:
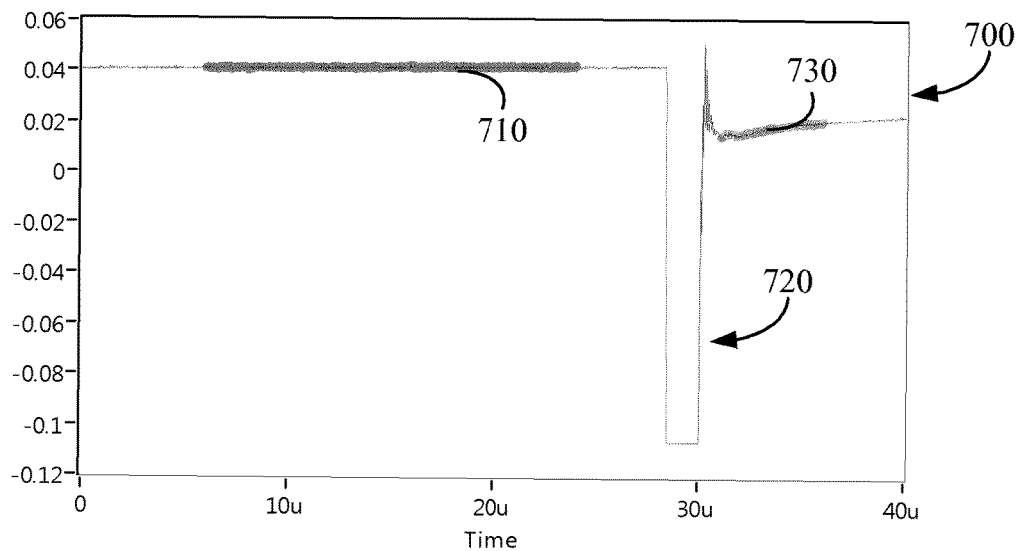
FIG. 7 is a graphical diagram of a magnetometer system using a reference signal acquisition prior to RF pulse excitation sequence and measured signal acquisition.

FIG. 7 depicts a graph 700 of a magnetometer system using a reference signal 710 acquisition prior to RF pulse excitation sequence 720 and measured signal 730 acquisition. A contrast measurement between the measured signal 730 and the reference signal 710 for a given pulsed sequence is then computed as a difference between a processed read-out fluorescence level from the measured signal acquisition 730 and a processed reference fluorescence measurement from the reference signal 710. The processing of the measured signal 730 and/or the reference signal 710 may involve computation of the mean fluorescence over each of the given intervals. The reference signal 710 is to compensate for potential fluctuations in the optical excitation power level, which can cause a proportional fluctuation in the measurement and readout fluorescence measurements. Thus, in some implementations the magnetometer includes a full repolarization between measurements with a reference fluorescence intensity (e.g., the reference signal 710) captured prior to RF excitation (e.g., RF pulse excitation sequence 720) and the subsequent magnetic b field measurement data 730. This approach may reduce sensor bandwidth and increase measurement noise by requiring two intensity estimates per magnetic b field measurement. For a DNV magnetometer, this means that it needs full repolarization of the ensemble diamond [NV] states between measurements. In some instances, the bandwidth considerations provide a high laser power density trade space in sensor design, which can impact available integration time and achievable sensitivity.

Figure 8:
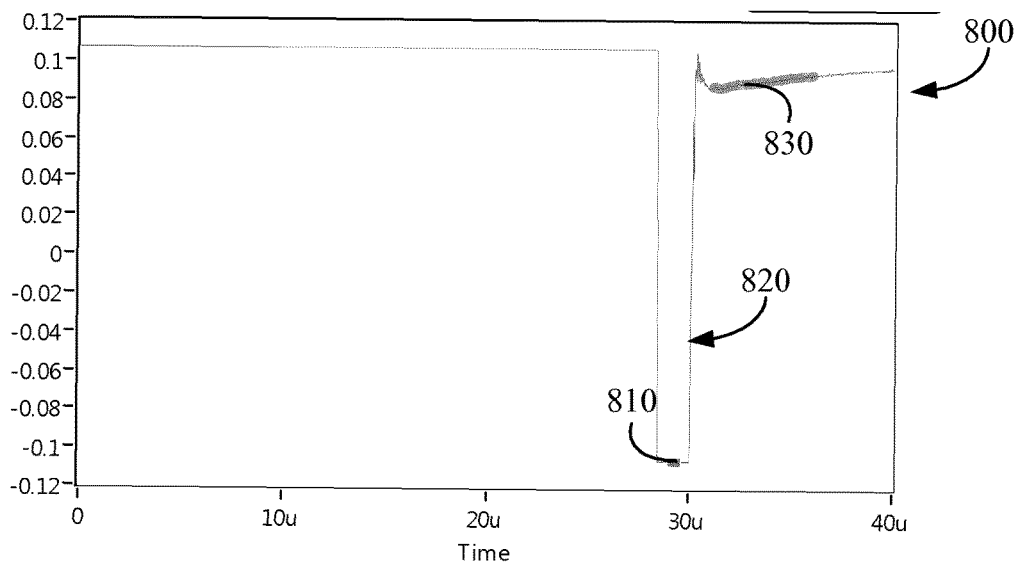
FIG. 8 is a graphical diagram of a magnetometer system omitting the reference signal acquisition of FIG. 6 prior to RF pulse excitation sequence and measured signal acquisition.

FIG. 8 depicts a graph 800 of a magnetometer system omitting a reference signal acquisition prior to RF pulse excitation sequence 820 and measured signal 830 acquisition. The RF pulse excitation sequence 820 may correspond to periods 1-3 of FIG. 6 and the measured signal acquisition 830 may correspond to period 4 of FIG. 6. The graph 800 depicts the amplitude of optical light emitted from a magneto-optical defect center material as measured by an optical detector 340, such as a photodiode, over time. The system processes the post RF sequence read-out measurement from the measured signal 830 directly to obtain magnetometry measurements. The processing of the measured signal 830 may involve computation of the mean fluorescence over each of the given intervals. In some implementations, a fixed "system rail" photo measurement is obtained and used as a nominal reference to compensate for any overall system shifts in intensity offset. In some implementations, an optional ground reference signal 810 may be obtained during the RF pulse excitation sequence 820, such as during period 2 of FIG. 6, to be used as an offset reference. Some embodiments provide faster acquisition times, reduced or eliminated noise from the reference signal, and increased potential detune intensity peak to peak contrast.

Figure 9:
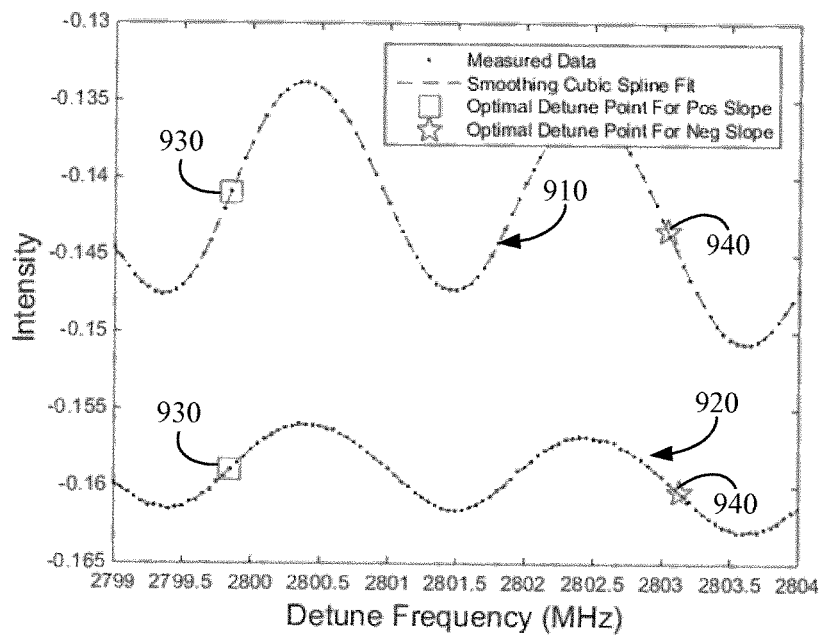
FIG. 9 is a graphical diagram depicting a reference signal intensity relative to detune frequency and a measured signal intensity relative to detune frequency.

FIG. 9 is a graphical diagram of an intensity of a measured signal 910 from an optical detector 340 relative to an intensity of a reference signal 920 from the optical detector 340 over a range of detune frequencies. When using a reference signal 920, the reference signal 920 will contain signal information from a prior RF pulse for a finite period of time. This prior signal information in the reference signal 920 reduces available detune peak to peak intensity range and slope for a detune point for positive slope 930 and a detune point for negative slope 940. That is, as shown in FIG. 9, the reference signal 920 is curved in a similar manner to the measured signal 910. Accordingly, when a reference signal 920 value is subtracted from a corresponding measured signal 910 at a corresponding detune frequency, the net magnetometry curve peak to peak intensity contrast is reduced. The reason that the reference signal 910 curve contains information from the measured signal 910 curve is due to insufficient (laser only) polarization time for a given sensor configuration. The prior RF pulse defines the state of the measurement and, if not enough time passes between measurements, then the reference signal 920 will contain some of the "hold" data from the prior RF "sample." This will subtract from the current measured signal 910, thereby resulting in less signal overall as seen in FIG. 9. Thus, to remove the prior signal information, the system would need to wait until the prior signal information is eliminated from the reference signal or operate without the reference signal, such as described herein. Prior signal information from a prior measured signal 910 (RF pulse) is cleared out via excitation from a green laser source and waiting for a period of time. This decay is exponential and tied to the power density applied from laser. However, waiting for a period of time for the prior signal information to be eliminated can decrease available bandwidth.

Figure 10:
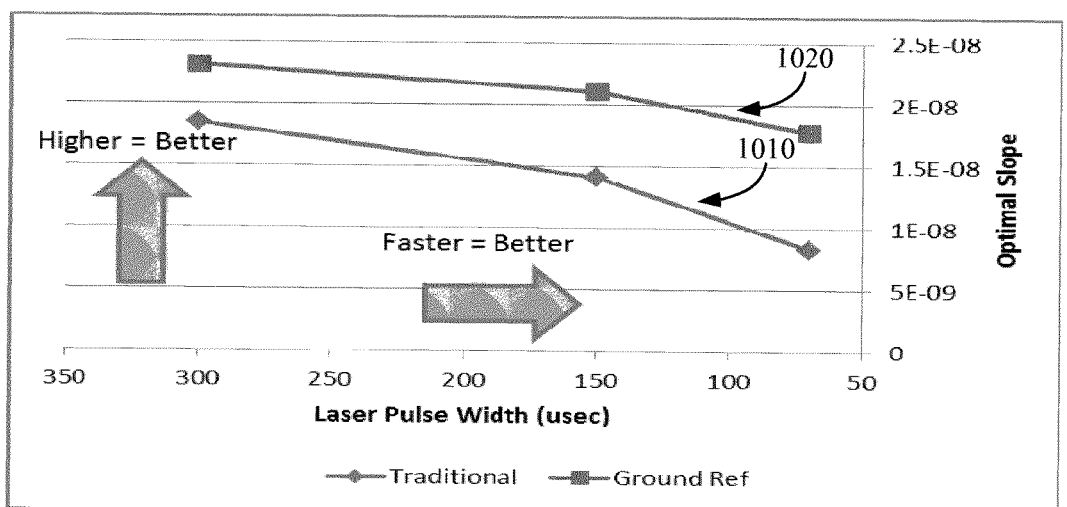
FIG. 10 is a graphical diagram depicting a slope relative to laser pulse width for a system implementing a reference signal and a system omitting the reference signal.

FIG. 10 is a diagram depicting slope relative to laser polarization pulse width for a system implementing a reference signal and a system omitting the reference signal. A first slope line 1010 corresponds to a system utilizing a reference signal while a second slope line 1020 corresponds to a system without utilizing a reference signal. As shown, the second slope line 1020 has a higher slope at equivalent laser pulse widths (in microseconds) compared to the first slope line 1010 that uses a reference signal. Longer polarization pulse widths can allow for a more complete repolarization of the a magneto-optical defect center material quantum state to reduce the residual impact of previous RF excitations. In effect, this more complete polarization can allow "less dimmed" fluorescence levels to be measured more accurately rather than exhibiting residual dimming due to an earlier RF excitation that retains some NV spin +1/−1 excited states. The wider measurement range can increase the peak to peak intensity range and, therefore, optimal slope. While both unreferenced first slope line 1010 and the referenced second slope line 1020 indicate a drop off in slope with shorter polarization pulse widths, the referenced second slope line 1020 decreases more quickly than the unreferenced first slope line 1010 due to the incomplete polarization of the reference, such as the reference signal 920 of FIG. 9, that is further subtracted from the measured signa, such as measured signal 910 of FIG. 9. As shown, the second slope line 1020 has a slower roll-off (e.g., reduction) of slope at shorter laser pulse widths than the first slope line 1010. That is, the lase pulse widths can be reduced without a significant decrease in optimal slope values. The second slope line 1020 can achieve a smaller laser pulse width of approximately 60-70 microseconds with minimal loss in slope compared to the first slope line 1010 that reduces slope by a factor of two when the laser pulse width is reduced by a factor of four. Thus, by eliminating the need for the reference signal, the second slope line 1020 demonstrates that the system can achieve an increase in sample rate by a factor of four with minimal impact on the slope point.

Figure 11:
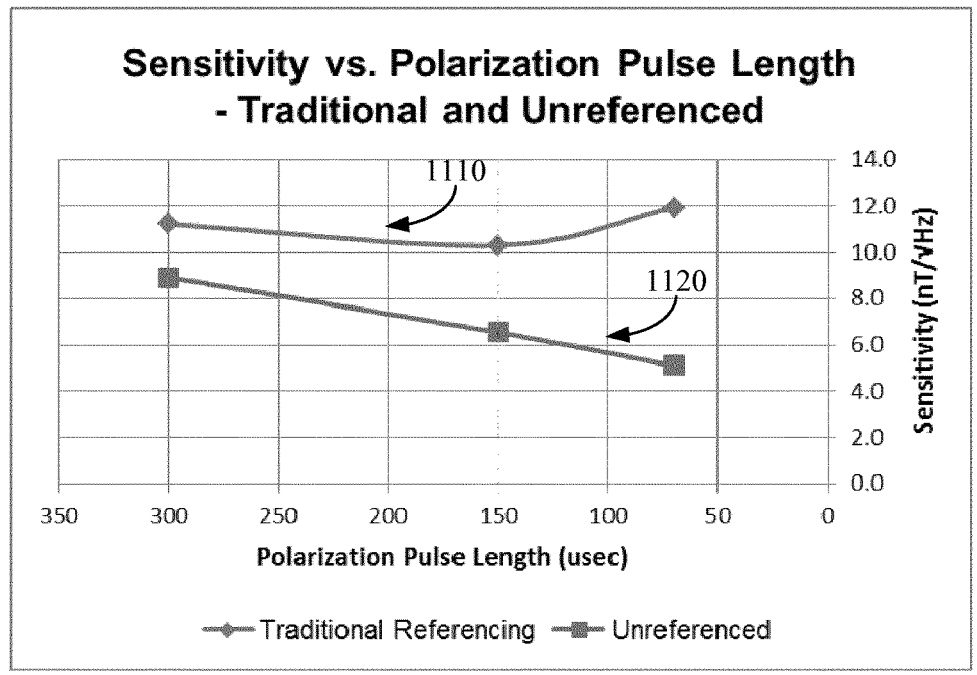
FIG. 11 is a graphical diagram depicting a sensitivity relative to polarization pulse length for a system implementing a reference signal and a system omitting the reference signal.

FIG. 11 depicts a comparison of a sensitivity of a system relative to a laser polarization pulse length for a system implementing a reference signal and a system omitting the reference signal. In the diagram shown, a first sensitivity line 1110 for the system implementing the reference signal has a lower sensitivity achievable at 10 nanoTeslas per root Hertz for a polarization pulse length of 150 microseconds. Thus, the system is limited in sampling rate based on a polarization pulse length of 150 microseconds as lower polarization pulse lengths reduce the sensitivity achievable to higher values. In comparison, a second sensitivity line 1120 for the system without the reference signal continues to increase the achievable lower sensitivity for lower polarization pulse lengths below 150 microseconds. Thus, by eliminating the reference signal, the sensitivity of the system can be improved for shorter polarization pulse lengths.

Figure 12:
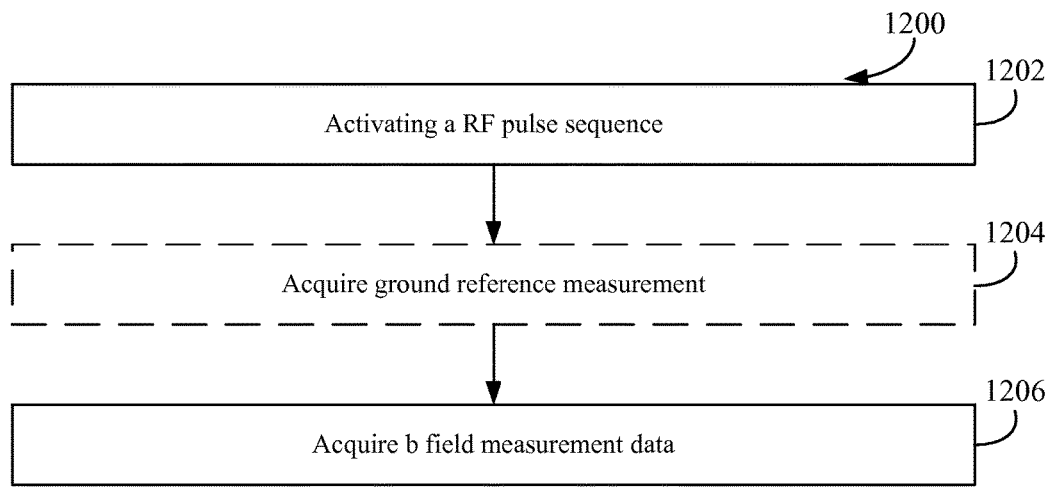
FIG. 12 is a process diagram for operating a magnetometer without using a reference signal.

FIG. 12 depicts some implementations of a process 1200 of operating a magnetometer that utilizes a magneto-optical defect center material, such as a diamond having nitrogen vacancies. The process 1200 includes activating an RF pulse sequence (block 1202). The RF pulse sequence is done without acquiring a reference measurement, thereby reducing measurement noise and increasing sample bandwidth by eliminating noise introduced by the reference measurement and decreasing the time between measurement acquisitions. In some implementations, a nominal ground reference measurement (block 1204) may be acquired as a simple offset relative to the ground state. The process 1200 further includes acquiring b field measurement data (block 1206). The acquisition of b field measurement data may be acquired at a faster sample rate as full repolarization of the magneto-optical defect center material is eliminated between measurements. In some implementations, the acquired b field measurement data may be processed to determine a vector of a measured b field. By removing the reference signal, a sensor can increase AC sensitivity and bandwidth.

Figure 13:
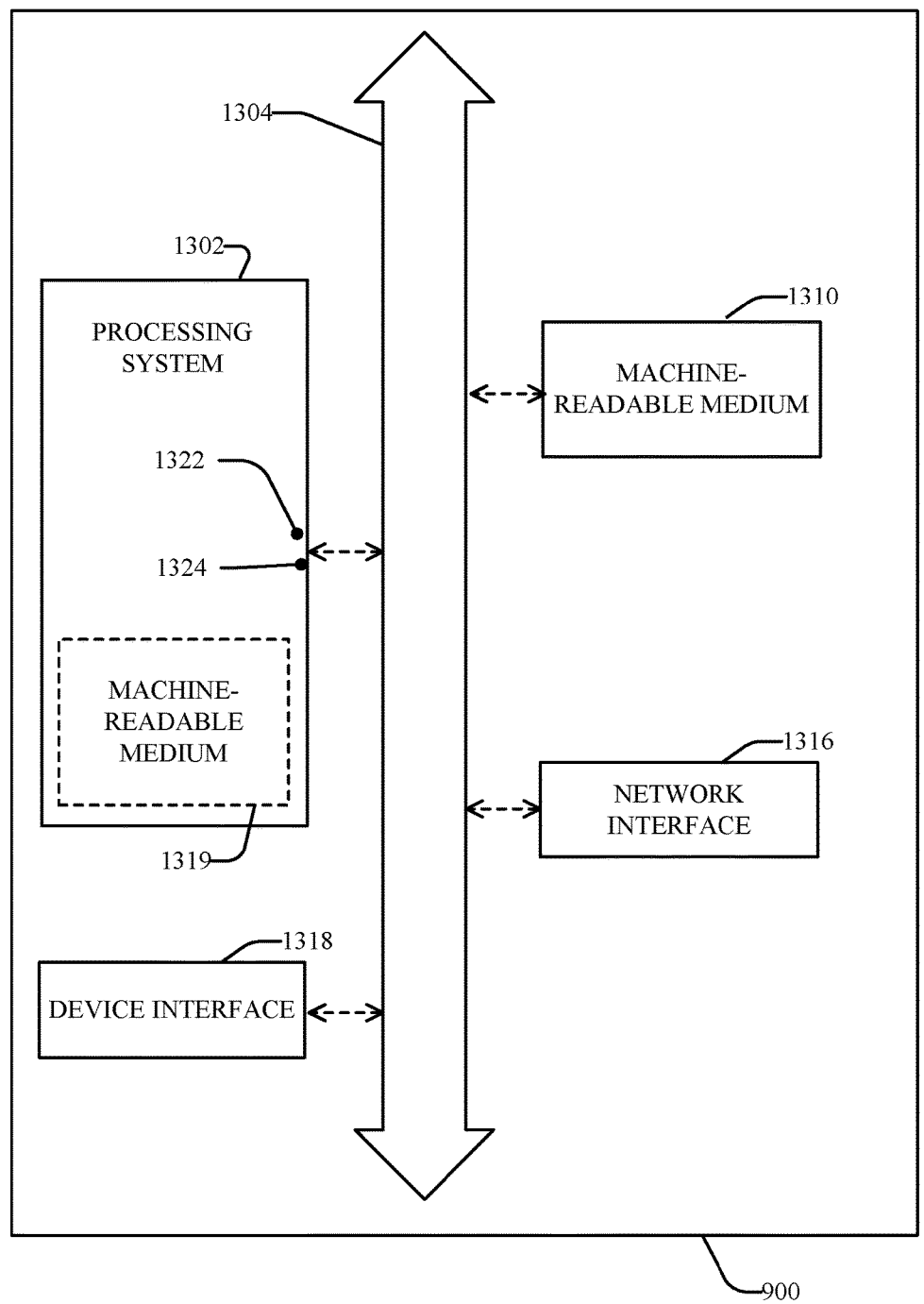
FIG. 13 is a block diagram depicting a general architecture for a computer system that may be employed to implement various elements of the systems and methods described and illustrated herein.

FIG. 13 is a diagram illustrating an example of a system 1300 for implementing some aspects such as the controller. The system 1300 includes a processing system 1302, which may include one or more processors or one or more processing systems. A processor may be one or more processors. The processing system 1302 may include a general-purpose processor or a specific-purpose processor for executing instructions and may further include a machine-readable medium 1319, such as a volatile or non-volatile memory, for storing data and/or instructions for software programs. The instructions, which may be stored in a machine-readable medium 1310 and/or 1319, may be executed by the processing system 1302 to control and manage access to the various networks, as well as provide other communication and processing functions. The instructions may also include instructions executed by the processing system 1302 for various user interface devices, such as a display 1312 and a keypad 1314. The processing system 1302 may include an input port 1322 and an output port 1324. Each of the input port 1322 and the output port 1324 may include one or more ports. The input port 1322 and the output port 1324 may be the same port (e.g., a bi-directional port) or may be different ports.

The processing system 1302 may be implemented using software, hardware, or a combination of both. By way of example, the processing system 1302 may be implemented with one or more processors. A processor may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device that can perform calculations or other manipulations of information.

A machine-readable medium may be one or more machine-readable media, including no-transitory or tangible machine-readable media. Software shall be construed broadly to mean instructions, data, or any combination thereof, whether referred to as software, firmware, middleware, microcode, hardware description language, or otherwise. Instructions may include code (e.g., in source code format, binary code format, executable code format, or any other suitable format of code).

Machine-readable media (e.g., 1319) may include storage integrated into a processing system such as might be the case with an ASIC. Machine-readable media (e.g., 1310) may also include storage external to a processing system, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device. Those skilled in the art will recognize how best to implement the described functionality for the processing system 1302. According to one aspect of the disclosure, a machine-readable medium is a computer-readable medium encoded or stored with instructions and is a computing element, which defines structural and functional interrelationships between the instructions and the rest of the system, which permit the instructions' functionality to be realized. Instructions may be executable, for example, by the processing system 1302 or one or more processors. Instructions can be, for example, a computer program including code for performing methods of some of the embodiments.

A network interface 1316 may be any type of interface to a network (e.g., an Internet network interface), and may reside between any of the components shown in FIG. 13 and coupled to the processor via the bus 1304.

A device interface 1318 may be any type of interface to a device and may reside between any of the components shown in FIG. 13. A device interface 1318 may, for example, be an interface to an external device (e.g., USB device) that plugs into a port (e.g., USB port) of the system 1300.

One or more of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. In one or more implementations, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more implementations, the computer readable media is non-transitory computer readable media, computer readable storage media, or non-transitory computer readable storage media.

In one or more implementations, a computer program product (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

While the above discussion primarily refers to microprocessor or multi-core processors that execute software, one or more implementations are performed by one or more integrated circuits, such as application specific integrated circuits (ASICs) or field programmable gate arrays (FPGAs). In one or more implementations, such integrated circuits execute instructions that are stored on the circuit itself.

In some aspects, some embodiments directed to magnetic band-pass filters for signals in magnetic communications and anomaly detection using diamond nitrogen-vacancy (DNV). In some aspects, some embodiments may be used in various markets, including for example and without limitation, advanced sensors and magnetic communication systems markets.

The description is provided to enable any person skilled in the art to practice the various embodiments described herein. While some embodiments have been particularly described with reference to the various figures and configurations, it should be understood that these are for illustration purposes only and should not be taken as limiting the scope of the subject technology.

There may be many other ways to implement. Various functions and elements described herein may be partitioned differently from those shown without departing from the scope of the subject technology. Various modifications to these embodiments may be readily apparent to those skilled in the art, and generic principles defined herein may be applied to other embodiments. Thus, many changes and modifications may be made by one having ordinary skill in the art, without departing from the scope of the subject technology.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various embodiments described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A system comprising:
a magnetometer including:
    a magneto-optical defect center material,
    an optical excitation source,
    a radiofrequency (RF) excitation source, and
    an optical sensor; and
a controller, the controller configured to:
    repetitively activate a radiofrequency (RF) pulse sequence for the RF excitation source to apply a RF field to the magneto-optical defect center material,
    repetitively activate an optical pulse sequence for the optical excitation source to apply a laser pulse to the magneto-optical defect center material, and
    repetitively acquire in conjunction with the optical pulse sequence a repetitive magnetic field measurement from the magneto-optical defect center material using the optical sensor, wherein the magnetic field measurement and the optical pulse sequence are performed repetitively in a continuous cycle independent of a reference magnetic field measurement.

2. The system of claim 1, wherein acquiring the repetitive magnetic field measurement comprises a polarization pulse length.

3. The system of claim 1, wherein the controller processes the repetitive magnetic field measurement directly to obtain magnetometry measurements.

4. The system of claim 1, wherein the controller is further configured to determine a vector of the repetitive magnetic field measurement.

5. The system of claim 1, wherein the controller uses a fixed system rail photo measurement as a nominal reference value.

6. The system of claim 1, wherein the magneto-optical defect center material is a diamond having nitrogen vacancies.

7. The system of claim 1, wherein the controller is further configured to process the magnetic field measurement.

8. A method for operating a magnetometer having a magneto-optical defect center material, the method comprising:
activating a radiofrequency (RF) pulse sequence to apply an RF field to the magneto-optical defect center material;
acquiring a nominal ground reference signal for the magneto-optical defect center material; and
acquiring a magnetic field measurement using the magneto-optical defect center material, wherein the magnetic field measurement is acquired independent of a reference magnetic field measurement.

9. The method of claim 8, wherein acquiring the magnetic field measurement comprises a polarization pulse length.

10. The method of claim 8, wherein acquiring a magnetic field measurement comprises processing the magnetic field measurement directly to obtain magnetometry measurements.

11. The method of claim 8 further comprising determining a vector of the repetitive magnetic field measurement.

12. The method of claim 8, wherein acquiring a magnetic field measurement comprises using a fixed system rail photo measurement as a nominal reference value.

13. The method of claim 8, wherein the magneto-optical defect center material is a diamond having nitrogen vacancies.

14. The method of claim 8 further comprising processing, using a controller, the magnetic field measurement.

15. A sensor comprising:
   a magneto-optical defect center material;
   a radiofrequency (RF) excitation source; and
   a controller configured to:
     activate a radiofrequency (RF) pulse sequence for the RF excitation source to apply a RF field to the magneto-optical defect center material,
     acquire a nominal ground reference signal for the magneto-optical defect center material, and
     acquire a magnetic field measurement from the magneto-optical defect center material, wherein the magnetic field measurement is acquired independent of a reference magnetic field measurement.

16. The sensor of claim 15, wherein acquiring the magnetic field measurement comprises a polarization pulse length.

17. The sensor of claim 15, wherein the controller processes the magnetic field measurement directly to obtain magnetometry measurements.

18. The sensor of claim 15, wherein the controller is further configured to determine a vector of the magnetic field measurement.

19. The sensor of claim 15, wherein the controller uses a fixed system rail photo measurement as a nominal reference value.

20. The sensor of claim 15, wherein the magneto-optical defect center material is a diamond having nitrogen vacancies.

* * * * *